United States Patent [19]

Nagano et al.

[11] Patent Number: 4,474,779

[45] Date of Patent: Oct. 2, 1984

[54] CEPHALOSPORIN COMPOUNDS

[75] Inventors: Noriaki Nagano; Kohji Nakano; Tadao Shibanuma; Yukiyasu Murakami, all of Saitama, Japan

[73] Assignee: Yamanouchi Pharmaceutical Co., Ltd., Tokyo, Japan

[21] Appl. No.: 433,247

[22] Filed: Oct. 7, 1982

Related U.S. Application Data

[63] Continuation-in-part of Ser. No. 364,226, Apr. 1, 1982, abandoned.

[30] Foreign Application Priority Data

Apr. 9, 1981 [JP] Japan .................................. 56/52408

[51] Int. Cl.$^3$ .................. A61K 31/545; C07D 501/56
[52] U.S. Cl. ..................................... 424/246; 544/26; 544/27; 548/213
[58] Field of Search ........................... 424/246; 544/27

[56] References Cited

U.S. PATENT DOCUMENTS 4,098,888 7/1978 Ochiai et al. ........................ 544/27
4,263,432 4/1981 Iwanami et al. ..................... 544/27

Primary Examiner—Paul M. Coughlan, Jr.
Attorney, Agent, or Firm—Burgess, Ryan & Wayne

[57] ABSTRACT

Cephalosporin compounds represented by the general formula

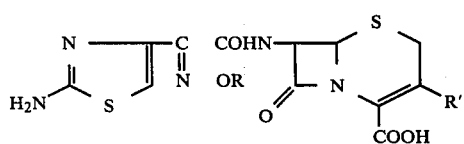

(wherein R represents a group shown by formula

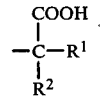

wherein $R^1$ represents a hydrogen atom or a lower alkyl group of 1–3 carbon atoms and $R^2$ represents a hydrogen atom, a lower alkyl group of 1–3 carbon atoms, a phenyl group which may be substituted by an amino or hydroxy group, a cyano group, a carboxy group, or a carboxymethyl group; said $R^1$ and $R^2$ may form a cycloalkylidene group of 4–6 carbon atoms together with the carbon atom to which they are bonded) or a group shown by formula $-CH_2-R^3$ (wherein $R^3$ represents a hydrogen atom, a halogenomethyl group, a carbamoyl group, a carboxymethyl group, α4-carboxy-3-hydroxyisothiazol-5-yl-thiomethyl group, or α2-carboxyphenylthiomethyl group); R' represents a group shown by formula $$-CH_2S-\underset{S}{\overset{R_a}{\underset{}{\bigvee}}}\overset{R_b}{\underset{N}{}}$$

(wherein $R_a$ represents a carboxy group, a cyano group, or a carbamoyl group which may be substituted by a lower alkyl group of 1–3 carbon atoms and $R_b$ represents a hydrogen atom or an amino group) or a group shown by formula $$-CH\underset{S}{\overset{S}{\underset{}{\bigvee}}}C=C\underset{\underset{NH}{\overset{\|}{C-R_b}}}{\overset{R_a}{}}$$

(wherein $R_a$ and $R_b$ have the same significance as above); and the waveline ~ shows an anti-form or syn-form bond and the salts thereof. They possess excellent antibacterial activities against gram positive bacteria and gram negative bacteria, in particular, pseudomonas aeruginosa and are useful as anti-bacterial agents.

8 Claims, No Drawings

CEPHALOSPORIN COMPOUNDS

CROSS-REFERENCE TO RELATED APPLICATION

This application is a continuation-in-part of co-pending application Ser. No. 364,226, filed Apr. 1, 1982, now abandoned.

FIELD OF THE INVENTION

This invention relates to novel cephalosporin compounds and the pharmaceutically acceptable salts thereof having excellent antibacterial activities against gram-positive bacteria and gram-negative bacteria.

BACKGROUND OF THE INVENTION

British Pat. No. 2,027,691 discloses cephalosporin antibiotics shown by the following general formula

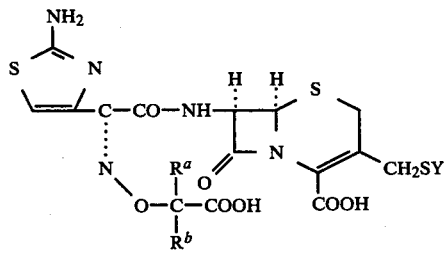

and it is described therein that these antibiotics are highly active to gram-negative bacteria. Also, Belgian Pat. No. 878,433 discloses amino-thiazolyl cephalosporin derivatives shown by the general formula

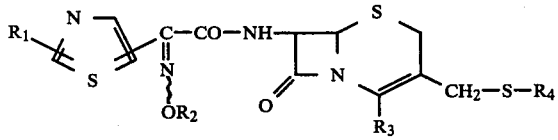

and it is described that they are active to gram-positive bacteria and gram-negative bacteria.

Furthermore, Belgian Pat. Nos. 853,545; 865,632; 866,038; 878,637; etc., disclose antibiotics having an α-thiazolyl-α-oximino-acetamido group as the substituent of the 7β-position of cephalosporin derivatives.

SUMMARY OF THE INVENTION

The object of this invention is to provide cephalosporin compounds having particularly substantial activities against pathogenic microorganisms by combining a specific novel substituent at the 3-position of cephalosporin compounds and a novel group or the specific group known by the above-described prior art at the 7β-position.

DETAILED EXPLANATION OF THE INVENTION

The present invention provides novel cephalosporin compounds represented by the following general formula I

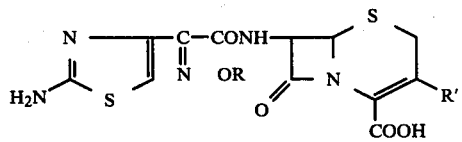

wherein R represents a group shown by

(wherein $R^1$ represents a hydrogen atom or a lower alkyl group of 1–3 carbon atoms and $R^2$ represents a hydrogen atom, a lower alkyl group of 1–3 carbon atoms, a phenyl group which may be substituted by an amino or hydroxy group, a cyano group, a carboxy group, or a carboxymethyl group; or $R^1$ and $R^2$ may form a cycloalkylidene group of 4–6 carbon atoms together with the carbon atom to which they are bonded) or a group shown by $-CH_2-R^3$ (wherein $R^3$ represents a hydrogen atom, a halogenomethyl group, a carbamoyl group, a carboxymethyl group, a 4-carboxy-3-hydroxyisothiazol-5-yl-thiomethyl group, or a 2-carboxyphenylthiomethyl group) and R' represents a group shown by

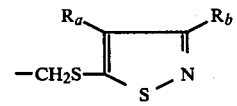

(wherein $R_a$ represents a carboxy group, a cyano group, or a carbamoyl group which may be substituted by an alkyl group of 1–3 carbon atoms and $R_b$ represents a hydroxy group or an amino group) or a group shown by the formula

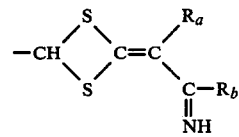

(wherein $R_a$ and $R_b$ have the same significance as above); and ~ represents an anti-form or syn-form bond and the salts thereof.

The term "a lower alkyl group of 1–3 carbon atoms" in the definition of the groups in the general formulae described in the specification means a straight or branched carbon chain having 1–3 carbon atoms. Thus, for example, the lower alkyl group of 1–3 carbon atoms includes a methyl group, an ethyl group, a propyl group, and an isopropyl group and the cycloalkylidene group of 4–6 carbon atoms includes a cyclobutylidene group, a cyclopentylidene group, and a cyclohexylidene group.

The invention also includes the pharmaceutically acceptable salts of the compounds shown by general formula I and as such salts, there are salts with inorganic bases, for example, an alkali metal such as sodium, potassium, etc., and an alkaline earth metal such as calcium, magnesium, etc.; ammonium salts; salts with organic bases or basic aminoacids such as trimethylamine, triethylamine, cyclohexylamine, dicyclohexylamine, diethanolamine, alginine, lysine, etc.; salts with mineral acids such as hydrochloric acid, sulfuric acid, phosphoric acid, etc.; and salts with organic acids such as acetic acid, lactic acid, tartaric acid, fumaric acid, maleic acid, methanesulfonic acid, ethanesulfonic acid, etc.

The compounds of this invention shown by formula I have an imino ether-type oxime and a 2-aminothiazole group in the 7β-substituent and hence there exist geometrical isomers and tautomers in these compounds. The invention includes all of these syn-form and anti-form geometrical isomers and the mutual tautomers.

The compounds of foregoing general formula I provided by the invention and the salts thereof are novel compounds having the feature of the chemical structure in the point that they have a (substituted isothiazol-5-yl)thiomethyl group or a substituted iminoalkylidenedithiethane-2-yl group at the 3-position of the cephalosporin skeleton. They possess excellent antibacterial activities against gram-positive bacteria and gram-negative bacteria, in particular, pseudomonas aeruginosa and are useful as antibacterial agents.

The antibacterial activities of the compounds of this invention are shown in the following table.

The compounds of this invention can be produced by various processes. The typical processes are shown below:

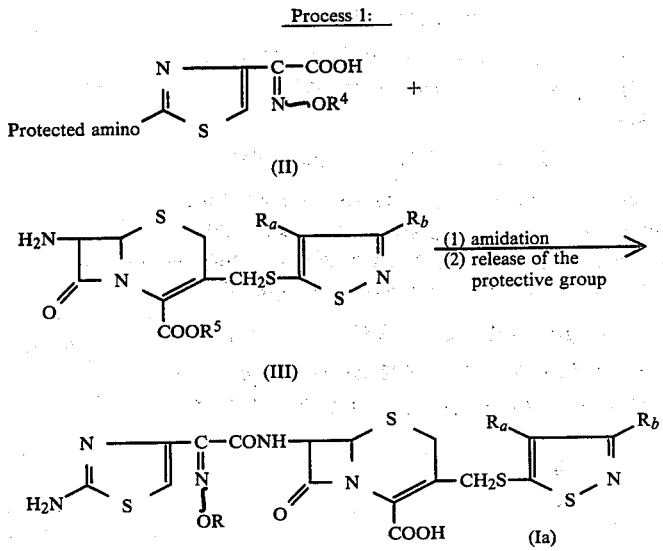

In the above reaction formula, $R^4$ represents group R having a protected carboxy group and $R^5$ represents a hydrogen atom or a protective group for a carboxy group. Among the compounds of this invention, a compound shown by general formula Ia can be produced by reacting the alkoxyiminothiazoleacetic acid derivative shown by general formula II or the reactive derivative thereof at a carboxy group with the 7-amino-3-isothiazolethiomethylcephalosporin derivative shown by general formula III, and then releasing the protective group of the amino group and/or carboxy group.

Practical examples of the protective group for the carboxy group are a trimethylsilyl group, a benzhydryl group, a β-methylsulfonylethyl group, a phenacyl group, p-methoxybenzyl group, a tert-butyl group, a p-nitrobenzyl group, etc., which can be easily released under a mild condition.

The forgoing reaction is usually performed in a solvent under cooling or at room temperature. There is no particular restriction about the solvent if the solvent does not take part in the reaction but organic solvents such as dioxane, tetrahydrofuran, ether, acetone,

| | Minimum Growth Inhibiting Concentration (μg/ml) | | | | | | | | | | | Known compounds* |
|---|---|---|---|---|---|---|---|---|---|---|---|---|
| | Example Number | | | | | | | | | | | |
| Organism | 2(ii) | 4(ii) | 6(ii) | 10(ii) | 14(ii) | 16(ii) | 17(ii) | 18(ii) | 26(ii) | 27(ii) | 28(ii) | |
| Kleb. pneumoniae ATCC 10031 | ≦0.2 | ≦0.2 | ≦0.2 | ≦0.2 | ≦0.2 | ≦0.2 | ≦0.2 | ≦0.2 | ≦0.2 | ≦0.2 | ≦0.2 | ≦0.2 |
| Sal. choleraesuis 1348 | ≦0.2 | ≦0.2 | ≦0.2 | ≦0.2 | — | — | — | — | — | — | — | 0.78 |
| Sh. sonnei II 37148 | ≦0.2 | 0.78 | ≦0.2 | ≦0.2 | 0.39 | ≦0.2 | 0.78 | ≦0.2 | ≦0.2 | ≦0.2 | ≦0.2 | 0.39 |
| Ps. aeruginosa IID 5142 | 1.56 | 0.39 | 1.56 | 1.56 | 0.78 | 1.56 | 3.13 | 0.39 | ≦0.2 | 1.56 | ≦0.2 | 12.5 |
| E. coli Ebara | ≦0.2 | 0.39 | ≦0.2 | ≦0.2 | ≦0.2 | ≦0.2 | ≦0.2 | ≦0.2 | ≦0.2 | ≦0.2 | ≦0.2 | 0.78 |
| Ent. aerogenes NY-2 | 0.78 | 3.13 | 3.13 | 0.39 | 3.13 | 1.56 | 1.56 | 1.56 | 0.78 | 1.56 | 0.78 | 3.13 |
| Ps. aeruginosa 99 | 0.78 | 3.13 | 1.56 | 0.78 | 3.13 | 3.13 | 6.25 | 0.78 | ≦0.2 | 1.56 | 0.39 | 12.5 |
| Ac. calcoaceticus IAM 12087 | 12.5 | 50 | 25 | 12.5 | 6.25 | 12.5 | 12.5 | 12.5 | 6.25 | 6.25 | 6.25 | 100 |

*(6R,7R)-7-[(Z)-2-(2-aminothiazol-4-yl)-2-(2-carboxy-prop-2-oximino)acetamido]-3-(1-methyltetrazol-5-yl-thiomethyl)ceph-3-em-4-carboxylic acid (the compound shown in British Patent No. 2,027,691).

methyl ethyl ketone, chloroform, methylene chloride, ethylene chloride, methanol, ethanol, acetonitrile, ethyl group for the amino group may be performed at the same time.

Process 2:

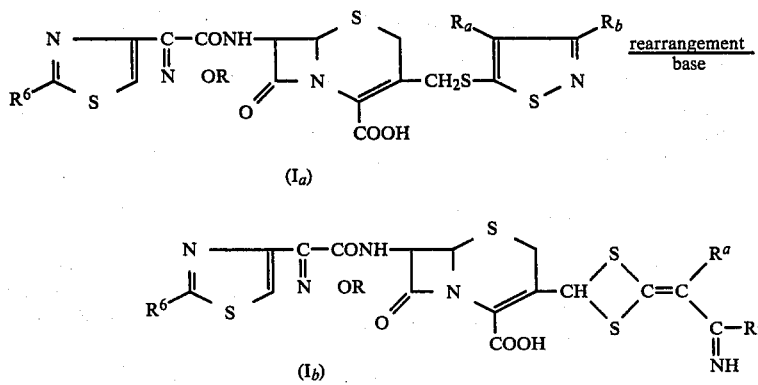

acetate, ethyl formate, dimethylformamide, dimethyl sulfoxide, etc., are usually used. These solvents may be used solely or as a mixture of them.

A compound of formula II is subjected to the reaction as the state of the free carboxylic acid or as the reactive derivative of the carboxylic acid. Suitable reactive derivatives are mixed as anhydrides, acid halides, active esters, active amides, acid anhydrides, acid azides, etc. When a compound of formula II is used as the state of the free carboxylic acid, a condensing agent such as N,N'-dicyclohexylcarbodiimide, N,N'-diethylcarbodiimide, etc., is used.

Also, according to the kind of the reaction derivative of the carboxylic acid used, it is sometimes preferred for proceeding smoothly, to conduct the reaction in the presence of a base. Examples of the base used in this case are inorganic bases such as sodium hydrogencarbonate, potassium hydrogen-carbonate, sodium carbonate, potassium carbonate, etc., and organic bases such as trimethylamine, triethylamine, dimethylaniline, pyridine, etc.

The removal of the protective group of the carboxy group from the product thus obtained can be easily performed by bringing the product into contact with an acid in the case of a benzhydryl group, a p-methoxybenzyl group, etc., or with water in the case of a trimethylsilyl group.

Also, the protective group for the amino group used in the course of producing a compound of this invention shown by formula Ia is a protective group usually used in the field of the peptide chemistry and, practically, there are, for example, acyl groups such as a formyl group, an acetyl group, a propionyl group, a tert-butoxycarbonyl group, a methoxyacetyl group, a methoxypropionyl group, a benzyloxycarbonyl group, a p-nitrobenzyloxycarbonyl group, etc., and aralkyl groups such as a benzyl group, a benzhydryl group, a trityl group, etc.

Furthermore, the removal of the protective group for the amino group can be easily performed by the hydrolysis with an acid when the foregoing aralkyl group such as a trityl group or various kinds of acyl groups are used as the protective group. As the acid used in this case, formic acid, trifluoroacetic acid, hydrochloric acid, etc., are preferred.

In addition, the removal of the protective group for the carboxy group and the removal of the protective In the reaction formula, $R^6$ represents an amino group or a protected amino group.

Also, the compound of this invention shown by general formula Ib can be produced by treating a compound shown by general formula Ia having a substituted isothiazol-5-yl-thiomethyl group at the 3-position of the cephalosporin skeleton with a base to rearrange the compound.

As the base suitably used in this reaction, there are weak basic materials such as sodium hydrogencarbonate, potassium hydrogencarbonate, sodium carbonate, triethylamine, etc.

This reaction is usually performed in a solvent at room temperature or under cooling. There is no particular restriction about the solvent if the solvent does not take part in the reaction but water or water-miscible solvents such as methanol, acetone, tetrahydrofuran, dimethyl sulfoxide, dimethylformamide, etc., are suitably used solely or as a mixture thereof.

The salt of the compound of this invention shown by general formula I can be produced by performing above-described Process 1 or Process 2 using previously the salt of the starting material, or can be produced by applying a salt-forming reaction conventionally used in the field of the art to the free compound produced by foregoing Process 1 or 2.

For example, the alkali metal salt of the compound can be produced by adding a n-butanol solution of an alkali of 2-ethylhexanoate to the free compound produced by Process 1 or 2 and then adding thereto an organic solvent having a different solubility, such as ether, ethyl acetate, etc.; the salt of the compound with an organic base or a basic aminoacid can be produced by adding to the free compound an equivalent amount or slightly excessive amount of an organic base or a basic aminoacid such as dicyclohexylamine, triethylamine, cyclohexylamine, diethanolamine, arginine, lysine, etc., to cause a reaction; and the ammonium salt of the compound can be produced by adding aqueous ammonia to the free compound.

The isolation and purification of a compound of this invention shown by formula I and the salt thereof can be performed by an ordinary method such as an extraction with an organic solvent, a crystallization, and a separation and purification by column chromatography.

The antibacterial agent containing a compound of this invention shown by general formula I or a salt thereof is prepared by a conventional method using a conventional pharmaceutical carrier or excipient. The antibacterial agent may be orally administered as tablets, pills, capsules, granules, etc., or parenterally administered by injections such as intravenous injection, intramuscular injection, etc., or as a suppository, etc. The doses are properly determined according to the condition of a disease, the age, sex, etc., of a patient, are usually 250–3000 mg per day for an adult, and the antibacterial agent is administered 2–4 times a day.

Then, the invention will be explained in more detail by the following examples. In addition, some of the starting materials shown in general formula II and III used for producing the compounds of this invention are novel compounds and hence the production processes of them and the properties thereof are described as reference examples.

REFERENCE EXAMPLE 1

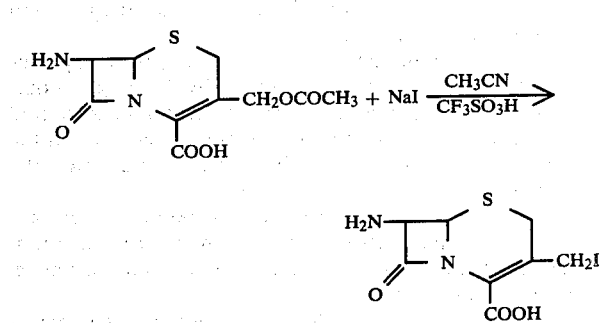

In a 20 milliliter three neck flask were placed 2.5 g (0.0092 mole) of 3-acetoxymethyl-7-amino-Δ³-cephem-4-carboxylic acid, 1.52 g of sodium iodide, and 12.5 ml of acetonitrile and the mixture was cooled until the inside temperature reached 18° C. Then, 5 ml of trifluoromethanesulfonic acid was added dropwise to the mixture at the same temperature as above over a 7 minute period. After conducting a reaction for 17 minutes at 12°–18° C., the reaction mixture was dispersed in 50 ml of ice water. The dispersion was stirred for 20 minutes under ice-cooling and then the formed crystals were recovered by filtration. The crystals thus obtained were washed with 32.5 ml of ice water and then 25 ml of acetone and dried over phosphorus pentaoxide in a dessicator to provide 2.09 g (yield of 67%) of 7-amino-3-iodomethyl-Δ³-cephem-4-carboxylic acid having a melting point of 177° C.

REFERENCE EXAMPLE 2

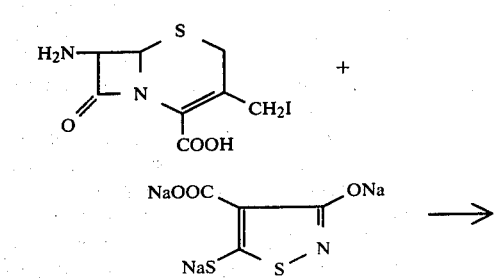

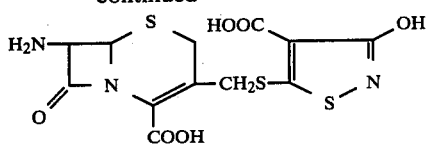

In 60 ml of water was suspended 3.4 g (0.01 mole) of 7-amino-3-iodomethyl-Δ³-cephem-4-carboxylic acid and then 0.84 g (0.01 mole) of sodium hydrogencarbonate was dissolved in the suspension. To the suspension was added 2.67 g (0.011 mole) of 4-carboxy-3-hydroxy-5-mercaptoisothiazole.trisodium salt and the mixture was reacted for 3 hours at room temperature. After the reaction was over, the pH of the reaction mixture was adjusted to 1.6 with 11.4 ml of 2N hydrochloric acid under ice-cooling. After stirring the reaction mixture for 10 minutes under ice-cooling, the precipitates thus formed were recovered by filtration. The precipitates were washed with 10 ml of cold water and dried to provide 2.9 g (yield of 74.5%) of 7-amino-3-[(4-carboxy-3-hydroxyisothiazol-5-yl)thiomethyl]-Δ³-cephem-4-carboxylic acid. About the melting point, the product began to discolor at about 170° C. and became black-brown at a temperature above 200° C.

Nuclear magnetic resonance spectra (in $D_2O + NaHCO_3$): δ(ppm): 3.58 (2H, q, $CH_2$ at 2-position) 3.98 (2H, q, $—CH_2—S—$) 5.04 (1H, d, CH at 6-position) 5.41 (1H, d, CH at 7-position)

Infrared absorption spectrum: $\nu_{max}^{KBr}$ cm$^{-1}$: 1770 (lactam)

REFERENCE EXAMPLE 3

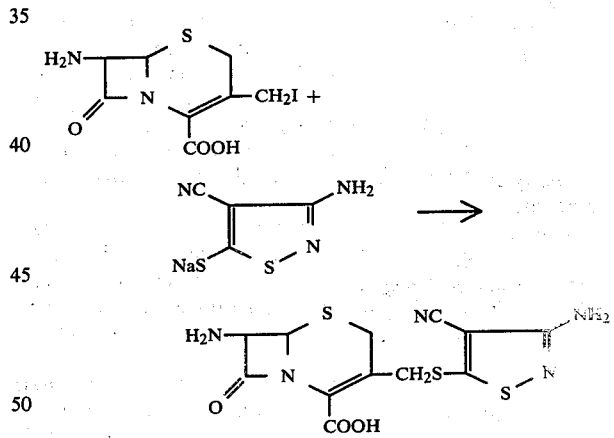

To 40 ml of an aqueous solution containing 0.7 g (0.0039 mole) of 3-amino-4-cyano-5-mercaptoisothazole sodium salt were added 1.2 g (0.0035 mole) of 7-amino-3-iodomethyl-Δ³-cephem-4-carboxylic acid and 0.29 g (0.0035 mole) of sodium hydrogencarbonate and the mixture was stirred for 3 hours at room temperature. Insoluble materials were filtered away using Perlite and the pH of the filtrate was adjusted to 2 with 2N hydrochoric acid under ice-cooling, After stirring the mixture for 10 minutes under ice-cooling, the precipitates thus formed were recovered with filtration, washed by 10 ml of water and dried under reduced pressure to provide 0.75 g of crude 7-amino-3-[(3-amino-4-cyanoisothiazol-5-yl)thiomethyl]Δ³-cephem-4-carboxylic acid.

The properties of the product purified were as follows:

Infrared absorption spectra: $\nu_{max}^{KBr}$ cm$^{-1}$: 2280, 1765, 1610

Nuclear magnetic resonance spectra (in D$_2$O—NaHCO$_3$): δ(ppm): 3.60 (2H, q) 4.18 (2H, q) 5.08 (1H, d) 5.42 (1H, d).

EXAMPLE 1

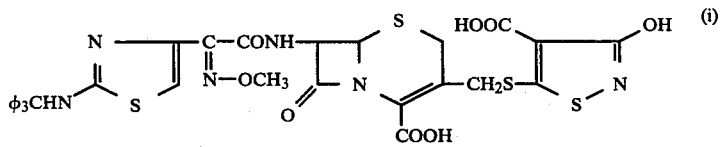

To 45 ml of dioxane were added 3.0 g (0.00677 mole) of (Z)-α-methoxyimino-α-(2-tritylaminothiazol-4-yl)acetic acid, 914 mg (0.00677 mole) of 1-hydroxybenztriazole and 1.42 g (0.00688 mole) of dicyclohexylcarbodiimide and the mixture was reacted for one hour at room temperature. After the reaction was over, the dicyclohexylurea precipitated and was filtered off to provide a dioxane solution of an active ester. On the other hand, 1.7 g (0.00437 mole) of 7-amino-3-[(4-carboxy-3-hydroxyisothiazol-5-yl)thiomethyl]-Δ$^3$-cephem-4-carboxylic acid obtained in Reference example 2 was suspended in 22 ml of water and then 1.0 g of sodium hydrogen-carbonate was slowly added thereto and dissolved. To the brown transparent solution thus obtained was added dropwise the foregoing dioxane solution of the active ester and the reaction was conducted for 4 hours at room temperature. After the reaction was over, the precipitated active ester was recovered from the reaction mixture by filtration (the recovered amount was 1.37 g). On the other hand, the filtrate was distilled under reduced pressure to remove dioxane therefrom and an aqueous solution of sodium hydrogen carbonate was added to the aqueous solution thus obtained to adjust the pH to 7.5-8. The aqueous solution was washed twice each time with 10 ml of ethyl acetate and 1N hydrochloric acid was added to the aqueous layer thus obtained to adjust the pH thereof to 1.5-2 (13 ml). To the acid aqueous solution were added 100 ml of methyl ethyl ketone and then 50 ml of methyl ethyl ketone to perform extraction. The unreacted starting material precipitated during extraction was removed by filtration. The methyl ethyl ketone solution was washed with 30 ml and then 20 ml of a saturated aqueous sodium chloride solution, dried by anhydrous magnesium sulfate, and distilled under reduced pressure to provide 4.4 g of a caramel material. The caramel material was subjected to silica gel column chromatography, eluted with a mixture of chloroform, isopropyl alcohol, and formic acid (90:10:2 in volume ratio), the fractions containing the desired product were collected, the solvent was distilled off, and the residue was powdered with ether to provide 1.5 g (yield of 28.5%) of (Z)-3-[(4-carboxy-3-hydroxyisothiazol-5-yl)thiomethyl]-7-[α-(methoxyimino)-α-(2-tritylaminothiazol-4-yl)acetamido]-Δ$^3$-cephem-4-carboxylic acid.

Infrared absorption spectrum: $\nu_{max}^{KBr}$ cm$^{-1}$: 1780 (lactam).

Nuclear magnetic resonance spectra (in d$_6$-DMSO): δ(ppm): 3.62 (2H, q, CH$_2$ at 2-position) 3.78 (3H, s, OCH$_3$) 4.14 (2H, q, —CH$_2$S—) 5.12 (1H, d, CH at 6-position) 5.56-5.76 (1H, q, CH at 7-position) 6.67 (1H, thiazole, CH at 5-position) 7.24-7.28 (15H, 3φ—) 8.74 (1H, s, —NH—) 9.48 (1H, d, —CONH—).

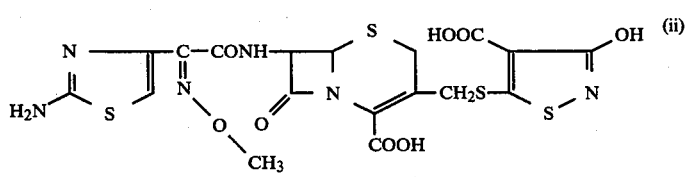

After cooling 4 ml of trifluoroacetic acid with ice water to a temperature below 5° C., 407 mg of the aforesaid compound was added thereto. The temperature rose to 6.5° C. during the addition. Then, 4 ml of water was added thereto and the reaction was conducted for one hour at a temperature below 10° C. Then, trifluoroacetic acid and water were distilled off under reduced pressure and the solid material thus formed was dissolved in 10 ml of ethanol. Then, ethanol was further partially distilled off and an oily product thus formed was powdered with ether to provide 300 mg of (Z)-7-[α-(2-aminophiazol-4-yl)-α-(methoxyimino)acetamido]-3-[(4-carboxy-3-hydroxyisothiazol-5-yl)thiomethyl]-Δ$^3$-cephem-4-carboxylic acid.

Infrared absorption spectrum: $\nu_{max}^{KBr}$ cm$^{-1}$: 1770 (lactam)

Nuclear magnetic resonance spectra (in d$_6$-DMSO): δ(ppm): 3.64 (2H, q, CH$_2$ at 2-position). 3.84 (3H, s, OCH$_3$) 4.18 (2H, q, —CH$_2$S—) 5.16 (1H, d, CH at 6-position) 5.72 (1H, s,

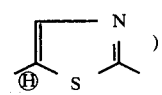

9.58 (1H, d, —NHCO—)

EXAMPLE 2

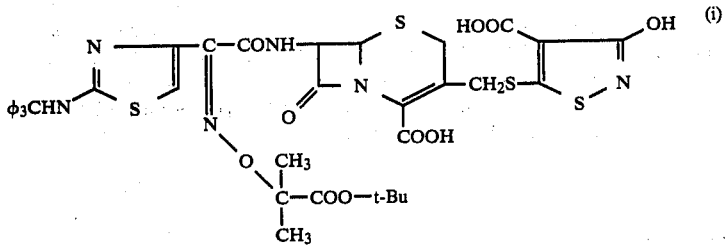

To 10 ml of dioxane were added 864 mg (0.0015 mole) of (Z)-α-(1-tert-butoxycarbonyl-1-methylethoxyimino)-α-(2-tritylaminothiazol-4-yl)acetic acid, 204 mg (0.0015 mole) of 1-hydroxybenztriazole, and 317 mg (0.0015 mole) of dicyclohexylcarbodiimide and the mixture was reacted for one hour at room temperature. After the reaction was over, dicyclohexylurea thus precipitated was removed by filtration to provide a dioxane solution of an active ester. On the other hand, 389 mg (0.001 mole) of 7-amino-3-[(4-carboxy-3-hydroxyisothiazol-5-yl)thiomethyl]-Δ$^3$-cephem-4-carboxylic acid was suspended in 4 ml of dimethyl sulfoxide and 390 μl of triethylamine was added thereto and dissolved. To the solution thus formed was added dropwise the dioxane solution of the active ester obtained in the aforesaid step at room temperature. After conducting the reaction for 4 hours at room temperature, dioxane was distilled off under reduced pressure, 20 ml of water and 2 ml of a saturated aqueous sodium hydrogen-carbonate solution were added to the reaction mixture, the mixture was washed twice each time with 20 ml of ethyl acetate, and after adjusting the pH of the aqueous layer to 1–1.5 with 2N hydrochloric acid, the precipitated products were extracted with 20 ml of methyl ethyl ketone. The methyl ethyl ketone solution was washed twice each time with 10 ml of a saturated aqueous sodium chloride solution, dried by anhydrous magnesium sulfate, and then the solvent was distilled off under reduced pressure to provide a solid residue. The solid residue was subjected to silica gel column chromatography with a mixture of chloroform, isopropyl alcohol, and formic acid (90:10:2 in volume ratio), and the fractions containing the desired product were collected. The solvent was distilled off under reduced pressure, and the residue was powdered by a mixture of ether and petroleum ether (1:1 in volume ratio) to provide 148 mg of (Z)-3-[(4-carboxy-3-hydroxyisothiazol-5-yl)thiomethyl]-7-[α-(2-tritylaminothiazol-4-yl)-α-(1-tert-butoxycarbonyl-1-methylethoxyimino)acetamido]-Δ$^3$-cephem-4-carboxylic acid.

Infrared absorption spectra: $\nu_{max}^{KBr}$ cm$^{-1}$: 1780, 1710–1720, 1670, 1500

Nuclear magnetic resonance spectra (in d$_6$-DMSO) δ(ppm): 1.88 (6H, s, —CH$_3$) 3.64 (2H, q, CH$_2$ at 2-position) 4.16 (2H, q, —CH$_2$S—) 5.15 (1H, d, CH at 6-position) 5.68 (1H, q, CH at 7-position) 6.66 (1H, s,

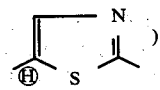

8.72 (1H, s, —NH—) 9.26 (1H, d, —NHCO—)

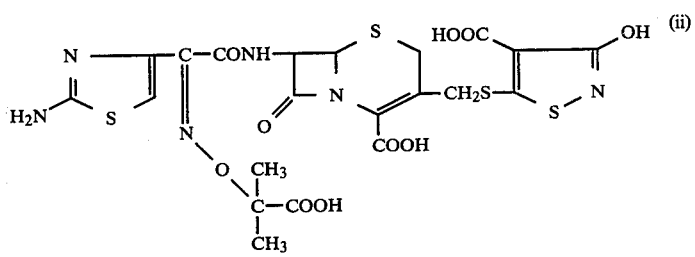

A mixture of 6 ml of trifluoroacetic acid and 0.5 ml of anisole was cooled by ice water and 555 mg of the aforesaid compound was added to the mixture. After allowing the mixture to react for one hour at 15°–20° C., 4 ml of water was added thereto and the reaction was further continued for one hour at 15°–20° C. After the reaction was over, trifluoroacetic acid, water, and anisole were distilled off under reduced pressure. Ethanol was added to the residue and the water was removed by azeotropic distillation with a part of ethanol. To the ethanol solution thus obtained, 10 ml of ether was added to provide powdered 360 mg of (Z)-7-[α-(2-aminothiazol-4-yl)-α-(1-carboxy-1-methylethoxyimino)acetamido]-3-[(4-carboxy-3-hydroxyisothiazol-5-yl)thiomethyl]-Δ$^3$-cephem-4-carboxylic acid.

Infrared absorption spectra: $\nu_{max}^{KBr}$ cm$^{-1}$: 1775, 1665

Nuclear magnetic resonance spectra (in d$_6$-DMSO): δ(ppm): 1.46 (6H, s, CH$_3$) 3.69 (2H, q, CH$_2$ at 2-position) 4.19 (2H, q, —CH$_2$S—) 5.21 (1H, d, CH at 6-position) 5.86 (1H, q, CH at 7-position) 6.77 (1H, s,

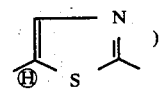

9.43 (1H, d, —NHCO—)

EXAMPLE 3

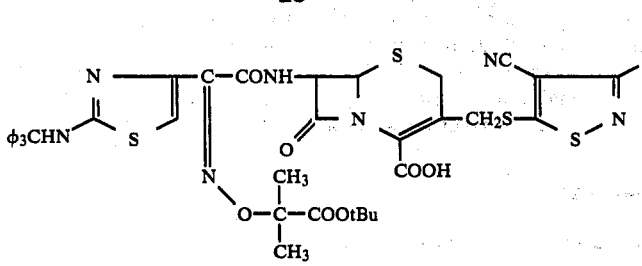

To 10 ml of dioxane were added 1.14 g (0.002 mole) of (Z)-α-(1-tert-butoxycarbonyl-1-methoxyethoxyimino)-α-(2-tritylaminothiazol-4-yl)acetic acid, 0.27 g (0.002 mole) of 1-hydroxybenztriazole and 0.41 g (0.002 mole) of dicyclohexylcarbodiimide, and the mixture was stirred for one hour at room temperature. The reaction mixture was filtered to remove dicyclohexylurea. The filtrate was added dropwise to a mixture of 0.75 g (0.002 mole) of 7-amino-3-[(3-amino-4-cyanoisothiazol-5-yl)thiomethyl]-Δ³-cephem-4-carboxylic acid obtained in Reference example 3, 0.24 g (0.0028 mole) of sodium hydrogencarbonate and 10 ml of water. After further adding 10 ml of dioxane and 10 ml of methyl ethyl ketone to the solution, the mixture was stirred overnight at room temperature. The reaction mixture was concentrated under reduced pressure to about 20 ml and after adding thereto 50 ml of water, insoluble materials were filtered off. On the filtrate was placed a layer of 100 ml of ethyl acetate and then after stirring the mixture under ice-cooling, the pH thereof was adjusted to 2 with 2N hydrochloric acid. The ethyl acetate layer was recovered, washed three times each time with 100 ml of a saturated aqueous sodium chloride solution, dried by anhydrous magensium sulfate, and concentrated under reduced pressure to provide 0.8 g of the powder of crude 3-[(3-amino-4-cyanoisothiazol-5-yl)thiomethyl]-7-[α-(1-tert-butoxycarbonyl-1-methylethoxyimino)-α-(2-tritylaminothiazol-4-yl)acetamido]-Δ³-cephem-4-carboxylic acid.

Infrared absorption spectra: $\nu_{max}^{KBr}$ cm$^{-1}$: 2205, 1775, 1720, 1680

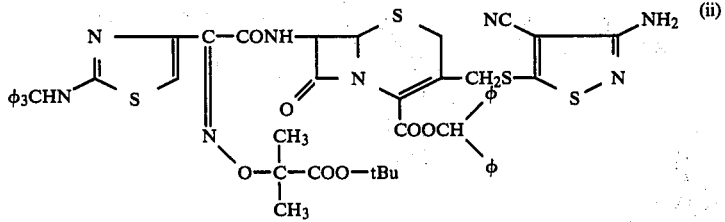

In 10 ml of methylene chloride was dissolved 0.8 g of the compound obtained in process (i) and after adding thereto 0.2 g of diphenyldiazomethane, the mixture was stirred for 3 hours at room temperature. The reaction mixture was concentrated, subjected to silica gel column chromatography, eluted with a mixture of benzene and ethyl acetate (85:15 in volume ratio), and the fractions containing the desired product were collected and concentrated to provide 200 mg of (Z)-3-[(3-amino-4-cyanoisothiazol-5-yl)thiomethyl]-7-[α-(1-tert-butoxycarbonyl-1-methylethoxyimino)-α-(2-tritylaminothiazol-4-yl)acetamido]-Δ³-cephem-4-carboxylic acid benzyhydryl ester.

Infrared absorption spectra $\nu_{max}^{KBr}$ cm$^{-1}$: 2205, 1785, 1720, 1685

Nuclear magnetic resonance spectra (in CDCl₃-CD₃OD) δ(ppm): 1.35 (9H, s), 1.60 (6H, s), 3.43 (2H, q), 4.95 (1H, d), 5.85 (1H, d), 6.70 (1H, s), 6.85 (1H, s).

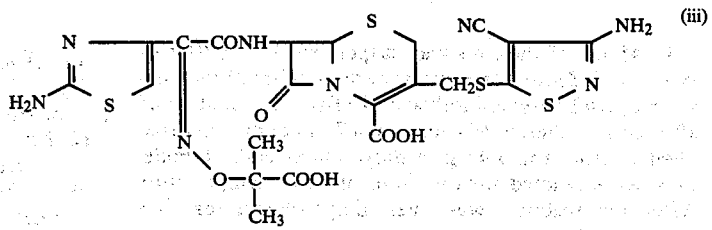

To 200 mg of the compound obtained in process (ii) were added 1 ml of anisole and 1 ml of trifluoroacetic acid under ice-cooling and the mixture was stirred for one hour at room temperature. The reaction mixture was concentrated under reduced pressure, the residue was treated with ether, and the powder thus obtained was recovered by filtration and dried. The powder thus obtained was dissolved in 1.5 ml of trifluoroacetic acid under ice-cooling and after adding thereto 0.5 ml of water, the mixture was stirred for one hour. The reaction mixture was concentrated under reduced pressure and treated with ether to form a powder, which was recovered by filtration, washed with ether, and dried under reduced pressure to provide 30 mg of (Z)-3-[(3-amino-4-cyanoisothiazol-5-yl)thiomethyl]-7-[α-(2-aminothiazol-4-yl)-α-(1-carboxy-1-methylethoxyimino)acetamido]-Δ³-cephem-4-carboxylic acid.

Infrared absorption spectra: $\nu_{max}^{KBr}$ cm$^{-1}$: 2205, 1770, 1670, 1620

Nuclear magnetic resonance spectra (in d$_6$-DMSO): δ(ppm): 1.44 (6H, s), 4.25 (2H, d), 5.18 (1H, d) 5.82 (1H, q), 6.71 (1H, s), 9.33 (1H, d)

EXAMPLE 4

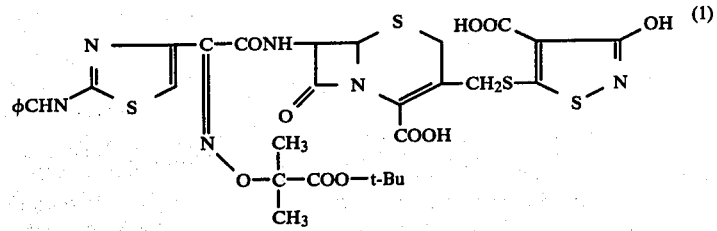

and

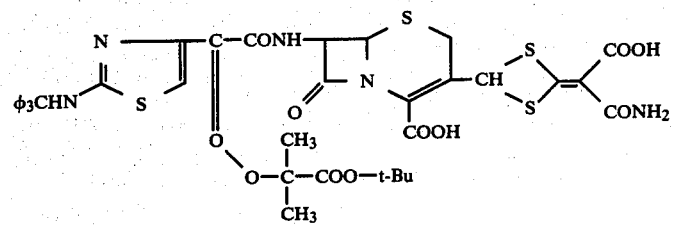

In 45 ml of dioxane was suspended 3.87 g (0.0067 mole) of (Z)-α-(1-tert-butoxycarbonyl-1-methylethoxyimino)-α-(2-tritylaminothiazol-4-yl)acetic acid and after adding thereto 914 mg (0.0067 mole) of 1-hydroxybenztriazole and 1.42 g of dicyclohexylcarbodiimide, they were reacted for one hour at room temperature. After the reaction was over, dicyclohexylurea thus precipitated was filtered away to provide a dioxane solution of an active ester. On the other hand, 1.7 g (0.00437 mole) of 7-amino-3-[(4-carboxy-3-hydroxyisothiazol-5-yl)thiomethyl]-Δ$^3$-cephem-4-carboxylic acid obtained in Reference example 2 was dissolved in 17 ml of dimethyl sulfoxide and then 1.5 ml of triethylamine was added to the solution under ice-cooling. After adding the foregoing dioxane solution of the active ester to the solution dropwise, the mixture was reacted for 3 days at room temperature. After the reaction was over, dioxane was distilled off under reduced pressure and the residue was dissolved in a mixture of 5 ml of water and 5 ml of an aqueous sodium hydrogencarbonate. The solution was washed twice with 20 ml and 10 ml of ethyl acetate and after placing 50 ml of methyl ethyl ketone in a layer on the aqueous layer, the mixture was acidified with 2N hydrochloric acid. Insoluble materials were filtered off and the aqueous layer was extracted again with 30 ml and 15 ml of methyl ethyl ketone. The organic layers were collected, washed well with a saturated aqueous sodium chloride solution, dried by anhydrous magnesium sulfate, and then methyl ethyl ketone was distilled off under reduced pressure to provide 3.5 g of a caramel material. The caramel material was subjected to silica gel column chromatography and then eluted with a mixture of chloroform, methanol, and formic acid (90:10:2 in volume ratio); the fractions containing the desired product were collected, and the solvents were distilled off to provide 640 mg of (Z)-3-[4-(1-carbamoyl-1-carboxymethylidene)-1,3-dithiethane-2-yl]-7-[α-(1-tert-butoxycarbonyl-1-methylethoxyimino)-α-(2-tritylaminothiazol-4-yl)acetamido]-Δ$^3$-cephem-4-carboxylic acid.

Infrared absorption spectra: $\nu_{max}^{KBr}$ cm$^{-1}$: 3360, 2970, 1780, 1720, 1665–1670, 1625, 1490, 1365, 1140

Nuclear magnetic resonance spectra (in d$_6$-DMSO): δ(ppm): 1.38 (9H, s, tBu) 3.90 (2H, s, CH$_2$ at 2-position) 5.12 (1H, d, CH at 6-position) 5.68 (1H, q, CH at 7-position) 5.70 (1H, s,

6.66 (1H, s,

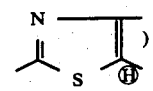

7.24–7.28 (15H, Cφ$_3$) 8.72 (1H, s, φ$_3$CH<u>N</u>—) 9.26 (1H, d, —CONH—)

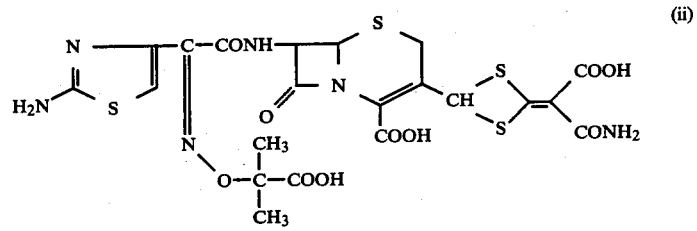

After cooling 5 ml of trifluoroacetic acid to 5° C., 640 mg of the foregoing compound was added thereto and the mixture was reacted for 60 minutes at 15°–17° C. and then was further reacted, after the addition of 2.5 ml of water under ice-cooling, for 60 minutes at 10°–15° C.

After the reaction was over, trifluoroacetic acid and water were distilled off under reduced pressure and the residue was dissolved in 3 ml of ethanol. Then, ethanol was partially distilled off under reduced pressure and the residue was powdered by the addition of 20 ml of ether followed by filtration. The powder thus obtained was washed well with ether and dried to provide 308 mg of (Z)-7-[α-(2-aminothiazol-4-yl)-α-(1-carboxy-1-methylethoxyimino)acetamido]-3-[4-(1-carbamoyl-1-carboxymethylidene)-1,3-dithiethane-2-yl]-Δ³-cephem-4-carboxylic acid.

Infrared absorption spectra: $\nu_{max}^{KBr}$ cm$^{-1}$: 3400, 1770, 1620–1680, 1480, 1355, 1260, 1180–1185, 1140.

Nuclear magnetic resonance spectra (in d₆-DMSO): δ(ppm): 1.46 (6H, s, —CH₃) 3.94 (2H, CH₂ at 2-position) 5.16 (1H, d, CH at 6-position) 5.71 (1H, s,

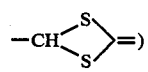

5.88 (1H, q, CH at 7-position) 6.62 (1H, s,

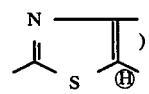

9.42 (1H, d, —CONH—)

EXAMPLE 5

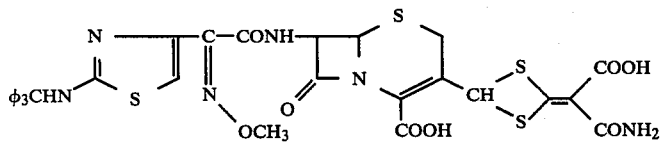

In 1 ml of dimethyl sulfoxide was dissolved 247 mg (0.0003 mole) of the compound obtained in Example 1-(i) and then 3 ml of dioxane was added to the solution. Then, after adding thereto 117 μl of triethylamine at room temperature, they were reacted for 3 days at room temperature. Dioxane was distilled off under reduced pressure from the reaction mixture, the residue obtained was mixed with 10 ml of water and dissolved therein with the addition of 0.5 ml of a saturated aqueous sodium hydrogencarbonate solution, and the solution thus obtained was washed in succession with 20 ml and 10 ml of ethyl acetate. On the aqueous layer was placed 20 ml of methyl ethyl ketone and after acidifying the mixture with 2N hydrochloric acid followed by extracting with methyl ethyl ketone, the aqueous layer was extracted with 10 ml of methyl ethyl ketone. The methyl ethyl ketone layers were combined with each other and washed with 10 ml of water and then 10 ml of a saturated sodium chloride solution. The resultant organic layer was dried with anhydrous magnesium sulfate and then methyl ethyl ketone was distilled off. The residue thus obtained was subjected to silica gel column chromatography, eluted with a mixture of chloroform, isopropyl alcohol, and formic acid (90:10:2 in volume ratio), and the fractions containing the desired product were collected and concentrated to provide 36 mg of (Z)-3-[4-(1-carbamoyl-1-carboxymethylidene)-1,3-dithiethane-2-yl]-7-[α-methoxyimino-α-(2-tritylaminothiazol-4-yl)acetamido]-Δ³-cephem-4-carboxylic acid.

Infrared absorption spectra: $\nu_{max}^{KBr}$ cm$^{-1}$: 3350, 2910, 1775, 1670, 1620, 1490, 1350–1380, 1260, 1020.

Nuclear magnetic resonance spectra (in d₆-DMSO): δ(ppm): 3.80 (3H, s, OCH₃) 3.84 (2H, s, CH₂ at 2-position) 5.12 (1H, d, CH at 6-position) 5.71 (1H, s,

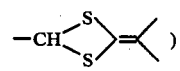

5.66–5.78 (1H, q, CH at 7-position) 6.72 (1H, s,

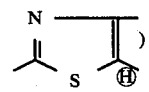

7.28 (15H, s, Cφ₃) 8.76 (1H, s, φ₃CNH—) 9.58 (1H, d, —NHCO—)

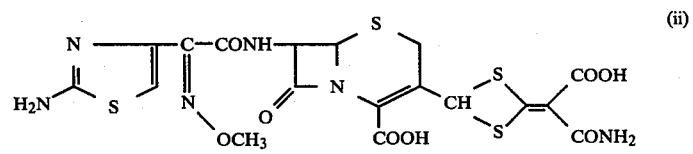

After cooling 3 ml of trifluoroacetic acid with ice water, 35 mg of the foregoing compound was added thereto. After dissolving the compound, 1.5 ml of water was added to the solution and the reaction was conducted for 60 minutes at 10°–15° C. After the reaction was over, water and trifluoroacetic acid were distilled off from the reaction mixture, the residue was dissolved in 3 ml of ethanol, ethanol was partially distilled off, and the residue was powdered by the addition of 10 ml of ether to the solution. After filtering, the powder was washed with ether to provide 23.3 mg of (Z)-7-[α-(2-aminothiazol-4-yl)-α-methoxyiminoacetamido]-3-[4-(1-carbamoyl-1-carboxymethylidene)-1,3-dithiethane-2-yl]-Δ³-cephem-4-carboxylic acid.

Infrared absorption spectra: $\nu_{max}^{KBr}$ cm$^{-1}$: 3300, 1870, 1770, 1660, 1620, 1480–1485, 1360–1380

Nuclear magnetic resonance spectra (in d₆-DMSO): δ(ppm): 3,84 (3H, s, OCH₃) 5.15 (1H, d, GH at 6-position) 5.71 (1H, s,

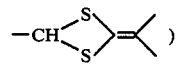

5.76 (1H, q, CH at 7-position) 6.65 (1H, s

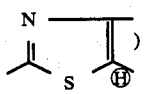

9.52 (1H, d, —CONH—)

EXAMPLE 6

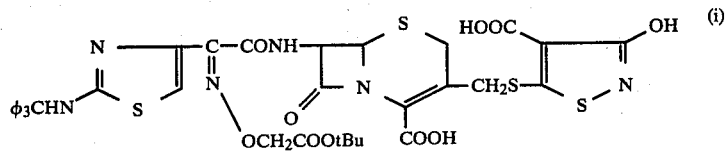

In 15.8 ml of dioxane was dissolved 1.23 g of (Z)-α-(tert-butoxycarbonylmethoxyimino)-α-(2-tritylamino-thiazol-4-yl)acetic acid, and 305 mg of 1-hydroxybenztriazole was added to the solution and then 510 mg of dicyclohexylcarbodiimide was added to the mixture. After stirring the reaction mixture for one hour at room temperature, dicyclohexylurea thus precipitated was fitlered off to provide a dioxane solution of an active ester. On the other hand, 580 mg of 7-amino-3[(4-carboxy-3-hydroxyisothiazol-5-yl)thiomethyl]-Δ$^3$-cephem-4-carboxylic acid was suspended in 7.5 ml of water and 252 mg of sodium hydrogencarbonate was slowly added thereto and dissolved in it. To the solution was added the foregoing dioxane solution of the active ester and they were reacted at 10°–15° C. After adding 9 ml of methyl ethyl ketone to the reaction mixture, the mixture was stirred for 5 hours at room temperature. The precipitate thus formed was filtered away from the reaction mixture and the filtrate was concentrated under reduced pressure. To the residue was added 40 ml of ethyl acetate, 20 ml of water, and 3 ml of a saturated aqueous sodium hydrogencarbonate solution, followed by separation of an aqueous layer and an organic layer. The pH of the aqueous layer thus obtained was adjusted to 1–2 with 1N hydrochloric acid and the product was extracted with 40 ml of methyl ethyl ketone. The methyl ethyl ketone solution was washed with 20 ml of a saturated aqueous sodium chloride solution, dried with anhydrous magnesium sulfate, and then the methyl ethyl ketone solution was concentrated under reduced pressure. The residue was subjected to silica gel column chromatography, eluted with mixture of chloroform, isopropyl alcohol, and formic acid (90:10:0.2 in volume ratio), and the fraction containing the desired product was collected. Then, the solvents were distilled off under reduced pressure to provide 170 mg of (Z)-7-[α-(tert-butoxycarbonylmethoxyimino)-α-(2-tritylamino-thiazol-4-yl)acetamido]-3-[(4-carboxy-3-hydroxyiso-thiazol-5-yl)thiomethyl]-Δ$^3$-cephem-4-carboxylic acid.

Infrared absorption spectrum: $\nu_{max}^{KBr}$ cm$^{-1}$: 1780

Nuclear magnetic resonance spectra (in d$_6$-DMSO) δ(ppm): 1.42 (9H, s, —t—Bu). 4.50 (2H, s,

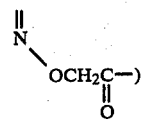

5.13 (1H, d, 5.69 (1H, 6.72 (1H, s,

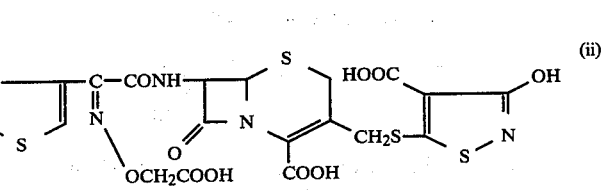

After adding 4 ml of trifluoroacetic acid to 170 mg of the compound obtained in process (i) under ice-cooling, the outer bath was maintained at 18° C. and the mixture was stirred for 1 hour. Then, after adding 2 ml of water to the reaction mixture under ice-cooling, the reaction mixture was further stirred for 1 hour while maintaining the outer bath at 18° C. and concentrated under reduced pressure. The residue was mixed with 10 ml of ethanol and the mixture was concentrated again under reduced pressure. To the residue was added 0.5 ml of ethanol to form a sticky product, which was powdered by the addition of 30 ml of ether to provide 100 mg of (Z)-7-[α-(2-aminothiazol-4-yl)-α-(carboxymethox-yimino)acetamido]-3-[4-carboxy-3-hydroxyisothiazol-5-yl)thiomethyl]-Δ$^3$-cephem-4-carboxylic acid.

Infrared absorption spectrum: $\nu_{max}^{KBr}$ cm$^{-1}$: 1760

Nuclear magnetic resonance spectra (in d$_6$-DMSO) δ(ppm): 3.64 (2H, q, 4.16 (2H, q, 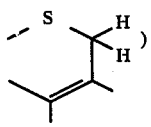

4.57 (2H, s, 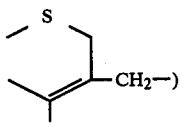

5.17 (1H, d, 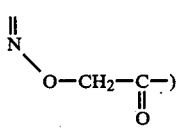

5.78 (1H, q, 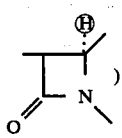

6.76 (1H, s, 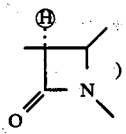

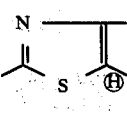

EXAMPLE 7

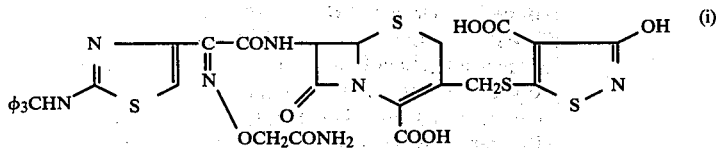

In 15 ml of dimethylformamide was dissolved 1.08 g of (Z)-α-(carbamoylmethoxyimino)-α-(2-tritylaminothiazol-4-yl)acetic acid and after adding thereto 319 mg of 1-hydroxybenztriazole and then 550 mg of dicyclohexylcarbodiimide, the mixture was stirred for one hour at room temperature. The resulting dicyclohexylurea precipitate was filtered away from the reaction mixture to provide a dimethylformamide solution of an active ester.

On the other hand, 580 mg of 7-amino-3-[(4-carboxy-3-hydroxyisothiazol-5-yl)thiomethyl]-Δ$^3$-cephem-4-carboxylic acid was suspended in 7.5 ml of water and 252 mg of sodium hydrogen-carbonate was slowly added thereto and dissolved.

To the solution was added the dimethylformamide solution of the active ester produced in the above step at 10°-15° C. and the mixture was stirred for 4 hours at room temperature. To the reaction mixture was added 70 ml of water and 50 ml of ethyl acetate and after separating an aqueous layer and an organic layer, the aqueous layer was adjusted to pH 1-2 with 1N hydrochloric acid and extracted with 100 ml of methyl ethyl ketone. The methyl ethyl ketone solution was washed with a saturated aqueous sodium chloride solution, dried with anhydrous magnesium sulfate, and concentrated under reduced pressure. The residue was subjected to silica gel column chromatography, eluted first with chloroform and then with a mixture of chloroform, isopropyl alcohol, and formic acid (90:5:0.2 in volume ratio), the fractions containing the desired product were collected, and the solvents were distilled off under reduced pressure to provide 70 mg of (Z)-7-[α-(carbamoylmethoxyimino)-α-(2-tritylaminothiazol-4-yl)acetamido]-3-[(4-carboxy-3-hydroxyisothiazol-5-yl)thiomethyl]-Δ$^3$-cephem-4-carboxylic acid.

Infrared absorption spectrum: $\nu_{max}^{KBr}$ cm$^{-1}$: 1768

Nuclear magnetic resonance spectra: δ(ppm): 4.38 (2H, s, 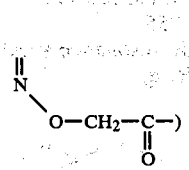

5.15 (1H, d, 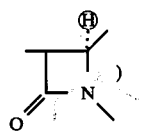

5.72 (1H, q, 

6.78 (1H, s, 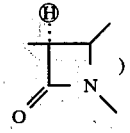

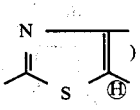

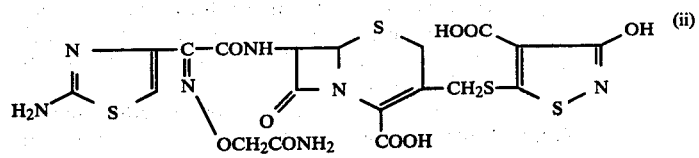

After dissolving 70 mg of the compound obtained in process (i) in 4 ml of trifluoroacetic acid under ice-cooling, 2 ml of water was added to the solution and the mixture was stirred for one hour at an outer temperature of 18° C. The reaction mixture was concentrated under reduced pressure; the residue obtained was mixed with 5 ml of ethanol, and the mixture was concentrated again under reduced pressure. To the residue was added 0.2 ml of ethanol to form a sticky product which was powdered by the addition of 20 ml of ether to provide 40 mg of (Z)-7-[α-(2-aminothiazol-4-yl)-α-(carbamoylmethoxyimino)acetamido]-3-[4-carboxy-3-hydroxyisothiazol-5-yl)thiomethyl]-Δ$^3$-cephem-4-carboxylic acid.

Infrared absorption spectrum:
$\nu_{max}^{KBr}$ cm$^{-1}$: 1755

Nuclear magnetic resonance spectra (in d$_6$-DMSO):
δ(ppm): 3.65 (2H, q,

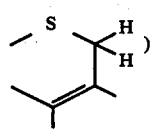

4.16 (2H, q,

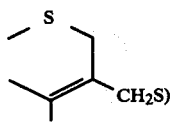

4.41 (2H, s,

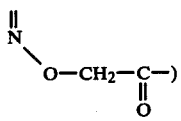

5.16 (1H, d,

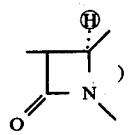

5.82 (1H, q,

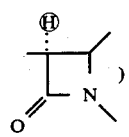

6.79 (1H, s,

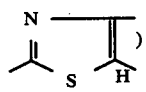

REFERENCE EXAMPLE 4

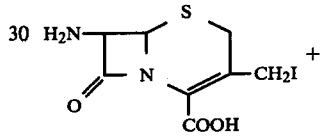

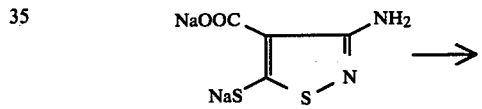

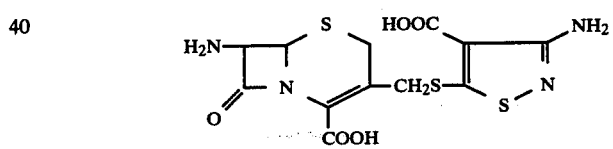

To 20 ml of liquid ammonia was added 1.2 g (0.006 mole) of 3-amino-4-carboxy-5-ethylthioisothiazole and then 450 mg of metallic sodium was added to the mixture at a temperature below −60° C. After distilling off liquid ammonia, the residual mixture was dried under reduced pressure and the residue was dissolved in 40 ml of water. Then, 1.2 g (0.0035 mole) of 7-amino-3-iodomethyl-Δ$^3$-cephem-4-carboxylic acid was added to the solution and the mixture was stirred for 3 hours at room temperature. The reaction mixture was filtered with Perlite to remove insoluble materials and the filtrate was adjusted to pH 2 with 2N hydrochloric acid under ice-cooling.

The precipitates thus formed were recovered by filtration, washed with water, and dried under reduced pressure to provide 1.4 g of crude 7-amino-3-[(3-amino-4-carboxyisothiazol-5-yl)thiomethyl]-Δ$^3$-cephem-4-carboxylic acid. The properties of the purified product are as follows:

Infrared absorption spectra: $\nu_{max}^{KBr}$ cm$^{-1}$: 1760, 1750, 1605

EXAMPLE 8

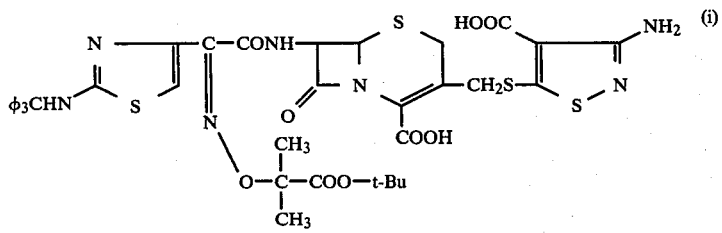

To 15 ml of dioxane were added 1.7 g (0.003 mole) of (Z)-α-(1-tert-butoxycarbonyl-1-methylethoxyimino)-α-(2-tritylaminothiazol-4-yl)acetic acid, 0.4 g (0.003 mole) of 1-hydroxybenztriazole, and 0.62 g (0.003 mole) of dicyclohexylcarbodiimide and then the mixture was stirred for one hour at room temperature. The reaction mixture was filtered to remove dicyclohexylurea and the filtrate was added dropwise to a mixture of 1.16 g (0.003 mole) of 7-amino-3-[(3-amino-4-carboxyisothiazol-5-yl)thiomethyl]-Δ³-cephem-4-carboxylic acid obtained in Reference example 4, 0.35 g (0.0042 mole) of sodium hydrogencarbonate, and 15 ml of water. After further adding 15 ml of dioxane to the mixture, the resultant mixture was stirred overnight at room temperature. To the reaction mixture was added 50 ml of water and insoluble materials were filtered off. On the filtrate was placed a layer of 100 ml of ethyl acetate and the pH of the mixture was adjusted to 2 with 2N hydrochloric acid with stirring under ice-cooling. The ethyl acetate layer was recovered, washed three times, each time with 100 ml of water, dried with anhydrous magnesium sulfate, and concentrated under reduced pressure to provide 0.6 g of the powder of crude 3-[(3-amino-4-carboxyisothiazol-5-yl)thiomethyl]-7-[α-(1-tert-butoxycarbonyl-1-methylethoxyimino)-α-(2-tritylaminothiazol-4-yl)acetamido]-Δ³-cephem-4-carboxylic acid.

Infrared absorption spectra:
$\nu_{max}^{KBr}$ cm$^{-1}$: 1775, 1720, 1675

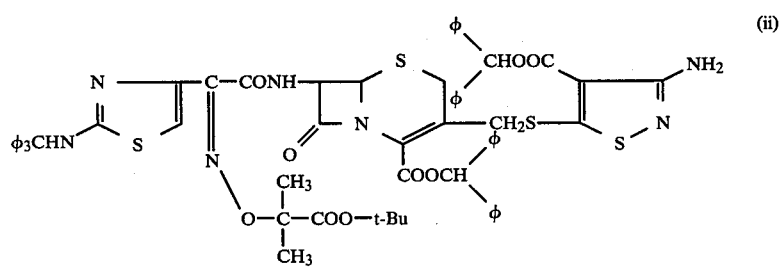

In 10 ml of methylene chloride was dissolved 0.6 g of the compound obtained in the above process and after adding thereto 0.2 g of diphenyldiazomethane, the mixture was stirred for 3 hours at room temperature. The reaction mixture was concentrated and the residue was subjected to silica gel column chromatography, eluted with a mixture of benzene and ethyl acetate (9:1 in volume ratio), and the fractions containing the desired product were collected and concentrated to provide 120 mg of (Z)-3-[(3-amino-4-diphenylmethoxycarbonylisothiazol-5-yl)thiomethyl]-7-[α-(1-tert-butoxycarbonyl-1-methylethoxyimino)-α-(2-tritylaminothiazol-4-yl)acetamido]-Δ³-cephem-4-carboxylic acid benzhydryl ester.

Infrared absorption spectra: $\nu_{max}^{KBr}$ cm$^{-1}$: 1775, 1715, 1680

Nuclear magnetic resonance spectra (in CDCl$_3$—CD$_3$OD): δ(ppm): 1.35 (9H, s) 1.60 (6H, s) 3.35 (2H, q) 4.95 (1H, d) 5.85 (1H, d) 6.25 (1H, s) 6.75 (2H, s)

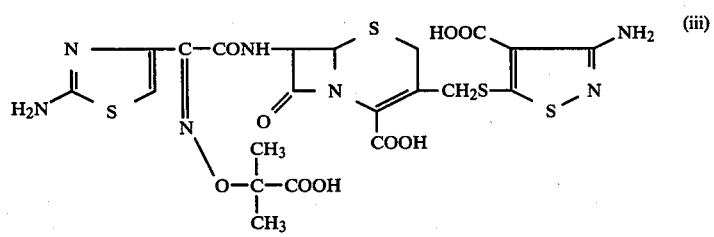

After adding 0.5 ml of anisole and 1 ml of trifluoroacetic acid to 120 mg of the compound obtained in the above process under ice-cooling, the mixture was stirred for 2 hours at room temperature. The reaction mixture was ice-cooled and after adding 0.4 ml of water to the reaction mixture, the mixture was stirred for 2 hours.

The reaction mixture was concentrated under reduced pressure and treated with ether to form a powder. The powder was recovered by filtration, washed with ether, and dried under reduced pressure to provide 50 mg of (Z)-3-[(3-amino-4-carboxyisothiazol-5-yl)thiomethyl]-7-[α-(2-aminothiazol-4-yl)-α-(1-carboxy-1-methylethoxyimino)acetamido]-Δ³-cephem-4-carboxylic acid.

Infrared absorption spectra: $\nu_{max}^{KBr}$ cm$^{-1}$: 1770, 1670

Nuclear magnetic resonance spectra (in d₆-DMSO): δ(ppm): 1.44 (6H, s) 5.18 (1H, d) 5.84 (1H, q) 6.72 (1H, s) 9.34 (1H, d)

REFERENCE EXAMPLE 8

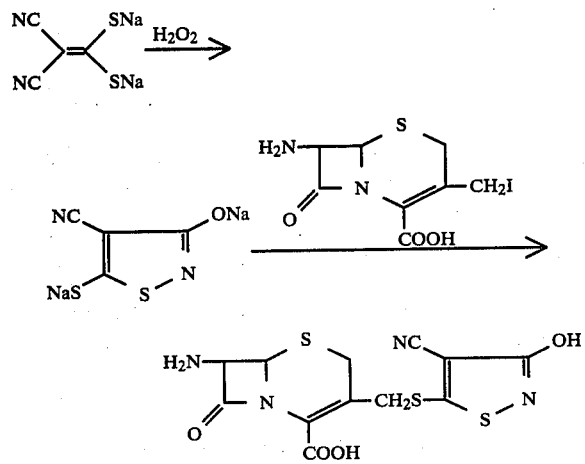

In 45 ml of ice water was dissolved 3.48 g (0.019 mole) of dimercaptomethylenepropanedinitrile disodium salt and then 3 ml of an aqueous 30% hydrogen peroxide solution was added dropwise to the solution at 0°–8° C. Thereafter, the mixture was further stirred for 3 hours at room temperature and after adding thereto 6.46 g (0.019 mole) of 7-amino-3-iodomethyl-Δ³-cephem-4-carboxylic acid and 1.6 g of sodium hydrogencarbonate, the resultant mixture was stirred for 3 hours at room temperature.

The reaction mixture was adjusted to pH 2.5 with 2N hydrochloric acid under ice-cooling and the solids thus precipitated were recovered by filtration, washed with water, and dried under reduced pressure to provide 4.1 g of crude 7-amino-3-[(3-hydroxy-4-cyanoisothiazol-5-yl)thiomethyl]-Δ³-cephem-4-carboxylic acid.

The properties of the purified product are as follows:

Infrared absorption spectra: $\nu_{max}^{KBr}$ cm⁻¹: 2205, 1780, 1610

Nuclear magnetic resonance spectra (in D₂O+NaHCO₃) δ(ppm): 3.58 (2H, q) 4.14 (2H, q) 5.05 (1H, d) 5.42 (1H, d)

EXAMPLE 9

To 15 ml of dioxane were added 1.33 g (0.003 mole) of (Z)-α-methoxyimino-α-(2-tritylaminothiazol-4-yl)acetic acid, 0.4 g (0.003 mole) 1-hydroxybenztriazole and 0.62 g (0.003 mole) of dicyclohexylcarbodiimide, and the mixture was stirred for one hour at room temperature. The reaction mixture was filtered to remove dicyclohexylurea. The filtrate was added dropwise to a mixture of 1.1 g (0.003 mole) of 7-amino-3-[(3-hydroxy-4-cyanoisothiazol-4-yl)thiomethyl]-Δ³-cephem-4-carboxylic acid, 0.35 g (0.0042 mole) of sodium hydrogencarbonate, and 15 ml of water. To the solution was further added 10 ml of dioxane and the mixture was stirred for 4 hours at room temperature. To the reaction mixture was added 40 ml of water and insoluble materials were filtered off. On the filtrate was placed a layer of 100 ml of ethyl acetate and the pH of the mixture was adjusted to 2 with 2N hydrochloric acid with stirring under ice-cooling. The ethyl acetate layer formed was recovered, washed with 100 ml of water, dried with anhydrous magnesium sulfate, and then concentrated under reduced pressure to provide 1.3 g of 3-[(4-cyano-3-hydroxyisothiazol-5-yl)thiomethyl]-7-[α-methoxyimino-α-(2-trithylaminothiazol-4-yl)acetamido]-Δ³-cephem-4-carboxylic acid.

Infrared absorption spectra: $\nu_{max}^{KBr}$ cm⁻¹: 2205, 1775, 1720, 1670

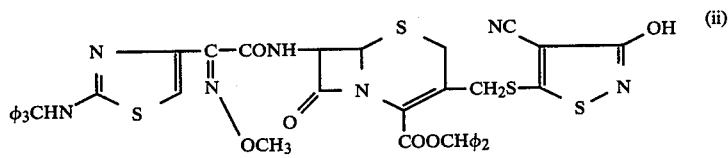

In 30 ml of methylene chloride was dissolved 1.3 g of the compound obtained in above process (i) and after adding thereto 400 mg of diphenyldiazomethane with stirring, the mixture was reacted for one hour at room temperature. The reaction mixture was concentrated and the residue was subjected to silica gel column chromatography, eluted with a mixture of benzene and ethyl acetate (9:1 in volume ratio), and the fractions containing the desired product were collected and concentrated to provide 490 mg of 3-[(4-cyano-3-hydroxyisothiazol-5-yl)thiomethyl]-7-[α-methoxyimino-α-(2-tritylaminothiazol-4-yl)acetamido]-Δ³-cephem-4-carboxylic acid benzhydryl ester.

Infrared absorption spectra: $\nu_{max}^{KBr}$ cm⁻¹: 2210, 1775, 1720, 1675

Nuclear magnetic resonance spectra (in CDCl₃—CD₃OD): δ(ppm): 3.40 (2H, q) 4.00(3H, s) 4.95 (1H,d) 5.85 (1H, d) 6.65 (1H, s) 6.90 (1H, s)

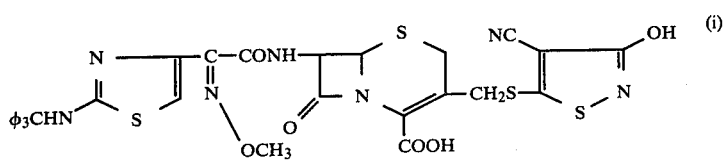

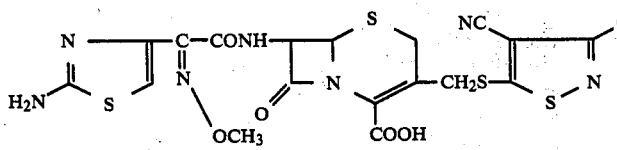

After adding 1 ml of anisole and 2 ml of trifluoroacetic acid to 480 mg of the compound obtained in above process (ii) under ice-cooling, the mixture was stirred for one hour and after further adding thereto 0.7 ml of water, the resultant mixture was further stirred for 1.5 hours. The reaction mixture was concentrated under reduced pressure and treated with ether to form a powder. The powder was recovered by filtration, washed with ether, and dried under reduced pressure to provide 210 mg of (Z)-7-[α-(2-aminothiazol-4-yl)-α-methoxyimino)acetamido]-3-[(4-cyano-3-hydroxyisothiazol-5-yl)thiomethyl]-Δ³-cephem-4-carboxylic acid.

Infrared absorption spectra. $\nu_{max}^{KBr}$ cm$^{-1}$: 2210, 1775

Nuclear magnetic resonance spectra (in d$_6$-DMSO): δ(ppm): 3.66 (2H, q) 3.84 (3H, s) 4.30 (2H, q) 5.14 (1H, d) 5.74 (1H, q) 6.72 (1H, s) 9.56 (1H, d)

EXAMPLE 10

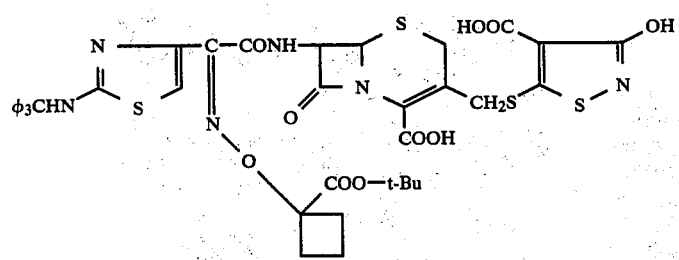

To 17.6 ml of dioxane was added 1.75 g (0.003 mole) of (Z)-2-(1-tert-butoxycarbonylcyclobut-1-oxyimino)-2-(2-tritylaminothiazol-4-yl)acetic acid, 405 mg (0.003 mole) of 1-hydroxybenztriazole, and 741 mg (0.0036 mole) of dicyclohexylcarbodiimide and the mixture was reacted for one hour at room temperature. After the reaction was over, dicyclohexylurea thus precipitated was filtered away to provide a dioxane solution of an active ester. On the other hand, 1.2 g (0.00308 mole) of 7-amino-3-[(4-carboxy-3-hydroxyisothiazol-5-yl)thi-omethyl]-Δ³-cephem-4-carboxylic acid was suspended in 10 ml of water and 518 mg of sodium hydrogencarbonate was slowly added thereto and dissolved in it. To the brown transparent solution thus obtained was added dropwise the aforesaid dioxane solution of the active ester and then the reaction was allowed to stand overnight at room temperature. The reaction mixture was distilled under reduced pressure to remove dioxane and to the residue was added 10 ml of water and 5 ml of a saturated aqueous sodium hydrogencarbonate solution. The mixture was washed twice each time with 30 ml of ethyl acetate. The aqueous layer thus formed was mixed with 7 ml of 2N hydrochloric acid and extracted with 100 ml and then 50 ml of methyl ethyl ketone. The unreacted starting materials precipitated during the procedure were filtered away. The methyl ethyl ketone solution was washed with 30 ml of water and then 30 ml of a saturated sodium chloride solution, dried by anhydrous magnesium sulfate, and the solvent was distilled off under reduced pressure to provide a caramel material. The caramel material was subjected to silica gel column chromatography, eluted with a mixture of chloroform, isopropyl alcohol, and formic acid (90:10:2), the fractions containing the desired product were collected, the solvents were distilled off, and the residue was powdered by the addition of ether to provide 526 mg of (Z)-3-[(4-carboxy-3-hydroxyisothiazol-5-yl)thiomethyl]-7-[α-(1-tert-butoxycarbonylcyclobut-1-yloxyimino)-α-(2-tritylaminothiazol-4-yl)acetamido]-Δ³-cephem-4-carboxylic acid.

Infrared absorption spectrum: $\nu_{max}^{KBr}$ cm$^{-1}$: 1770 (lactam)

Nuclear magnetic resonance spectra (in d$_6$-DMSO): δ(ppm): 1.38 (9H, s, —t—Bu) 3.64 (2H, q, CH$_2$ at 2-position) 4.16 (2H, q, —CH$_2$—S—) 5.17 (1H, d, CH at 6-position) 5.72 (1H, q, CH at 7-position) 6.66 (1H, s, thiazole at 5-position) 7.24 (15H, 3φ—) 8.76 (1H, s, —NH—) 9.34 (1H, d, —CONH—)

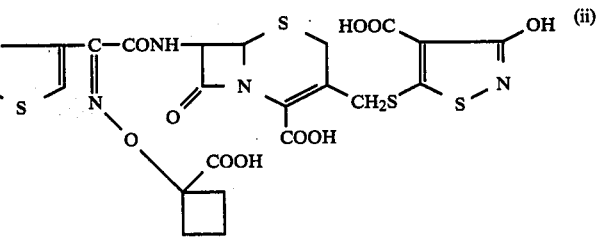

To 10 ml of trifluoroacetic acid was added 520 mg of the aforesaid compound and the mixture was reacted for one hour at 17°–19° C. After the reaction was over, the reaction mixture was cooled to about 10° C. and 5.6 ml of water was added dropwise to the reaction mixture at a temperature below 17° C. Thereafter, the mixture was further reacted for one hour at 15°–19° C. Then, trifluoroacetic acid and water were distilled off under reduced pressure from the reaction mixture and the residue was dissolved in 10 ml of ethanol. The ethanol was partially distilled off to provide an oily product which was powdered by the addition of ether to provide 354 mg of (Z)-7-[α-(2-aminothiazol-4-yl)-α-(1-carboxycyclobut-1-yloxyimino)acetamido]-3-[(4-carboxy-3-hydroxyisothiazol-5-yl)]-Δ³-cephem-4-carboxylic acid.

Infrared absorption spectrum: $\nu_{max}^{KBr}$ cm$^{-1}$: 1765 (lactam) Nuclear magnetic resonance spectra (in d$_6$-DMSO): δ(ppm): 1.89, 2.40 (6H, m, cyclobutane ring) 3.69 (2H, q, CH$_2$ at 2-position) 4.19 (2H, q, —CH$_2$S—) 5.23 (1H, d, CH at 6-position) 5.87 (1H, q, CH at 7-position) 6.77 (1H, s, thiazole at 5-position) 9.52 (1H, d, —CONH—)

EXAMPLE 11

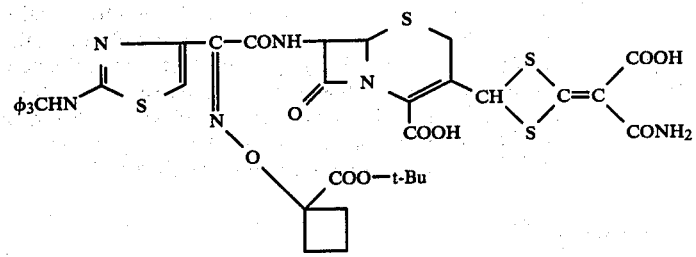

To 12 ml of dioxane was added 1.14 g (0.002 mole) of (Z)-2-(1-tert-butoxycarbonylcyclobut-1-yloxyimino)-2-(2-tritylaminothiazol-4-yl)acetic acid, 264 mg (0.002 mole) of 1-hydroxybenztriazole and 482 mg (0.0023 mole) of dicyclohexylcarbodiimide and the mixture was reacted for one hour at room temperature. After the reaction was over, dicyclohexylurea thus precipitated was filtered off to provide a dioxane solution of an active ester. On the other hand, 778 mg (0.002 mole) of 7-amino-3-[(4-carboxy-3-hydroxyisothiazol-5-yl)thiomethyl]-Δ³-cephem-4-carboxylic acid was suspended in 8 ml of dimethylsulfoxide and 836 μl of triethylamine was added thereto and dissolved at a temperature below 20° C. To the solution was added dropwise the aforesaid dioxane solution of the active ester and thereafter, the mixture was allowed to stand for 3 days at room temperature.

After the reaction was over, dioxane was distilled off under reduced pressure from the reaction mixture. the residue was dissolved in a mixture of 30 ml of water and 5 ml of a saturated aqueous sodium hydrogencarbonate solution, and the solution was washed with 50 ml of ethyl acetate. Then, 50 ml of methyl ethyl ketone was placed a layer on the aqueous layer thus formed and the mixture was acidified by the addition of 12 ml of 2N hydrochloric acid. Insoluble materials were filtered off and the organic layer was recovered. The aqueous layer was extracted further with 30 ml and 15 ml of methyl ethyl ketone. The organic layers were collected, washed with 30 ml of water and then 30 ml of a saturated aqueous sodium chloride solution, dried with anhydrous magnesium sulfate, and then methyl ethyl ketone was distilled off under reduced pressure to provide 1.54 g of a caramel material. The caramel material was subjected to silica gel column chromatography, eluted with a mixture of chloroform, isopropyl alcohol, and formic acid (90:10:2 in volume ratio), the fractions containing the desired product were collected, and the solvents were distilled off to provide 464 mg of (Z)-3-[-4-(1-carbamoyl-1-carboxymethylene)-1,3-diethiethan-2-yl]-7-[α-(1-tert-butoxycarbonylcyclobut-1-yloxyimino)-2-(2-tritylamino)thiazol-4-yl)acetamido]-Δ³-cephem-4-carboxylic acid.

Infrared absorption spectra: $\nu_{max}^{KBr}$ cm$^{-1}$: 3300–3350, 2950, 1770, 1720, 1670, 1620, 1485, 1360, 1135, 690.

(i)

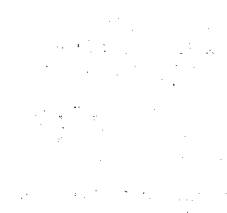

Nuclear magnetic resonance spectra (in d$_6$-DMSO): δ(ppm): 1.39 (9H, s, —t—Bu) 1.80–2.40 (6H, m, cyclobutane ring) 3.92 (2H, s, CH$_2$ at 2-position) 5.16 (1H, d, CH at 6-position) 5.70 (1H, s,

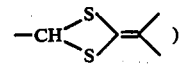

5.70–5.90 (1H, q, CH at 7-position) 6.67 (1H, s,

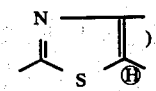

7.10–7.40 (15H, Cφ$_3$) 8.78 (1H, s, —NH—) 9.3–9.5 (1H, d, —CONH—)

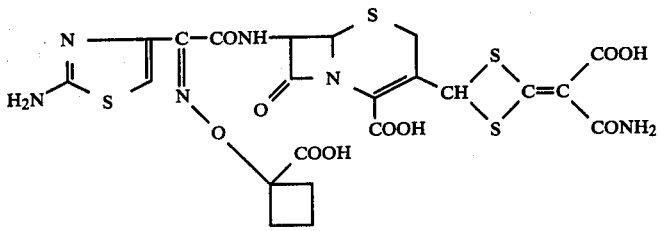

(ii)

After ice-cooling 10 ml of trifluoroacetic acid to a temperature below 10° C., 460 mg of the aforesaid compound was added thereto. Thereafter, 6.4 ml of water was added to the mixture at 17°–19° C. for 60 minutes and then under ice-cooling, and the mixture was reacted for 60 minutes at 17°–19° C. After the reaction was over, trifluoroacetic acid and water were distilled off under reduced pressure and to the residue thus obtained was added 10 ml of ethanol. Ethanol was partially distilled off to provide an oily product, which was powdered by the addition of 10 ml of ether and then 10 ml of n-hexane to provide 357 mg of (Z)-7-[α-(2-aminothiazol-4-yl)-α-(1-carboxycyclobut-1-yloxyimino)acetamido]-3-[4-(carbamoylcarboxymethylene)-1,3-dithiethan-2-yl]-Δ³-cephem-4-carboxylic acid.

Infrared absorption spectra: $\nu_{max}^{KBr}$ cm$^{-1}$: 3300, 2940, 1760, 1580–1680, 1480, 1370, 1250, 1140

Nuclear magnetic resonance spectra (in d$_6$-DMSO): δ(ppm): 1.92, 2,38 (6H, cyclobutane ring) 3.96 (2H, s, CH$_2$ at 2-position) 5.18 (1H, d, CH at 6-position) 5.73 (1H, s,

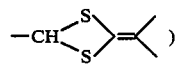

5.91 (1H, q, CH at 7-position) 6.74 (1H, s,

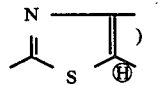

9.51 (1H, d, —CONH—)

EXAMPLE 12

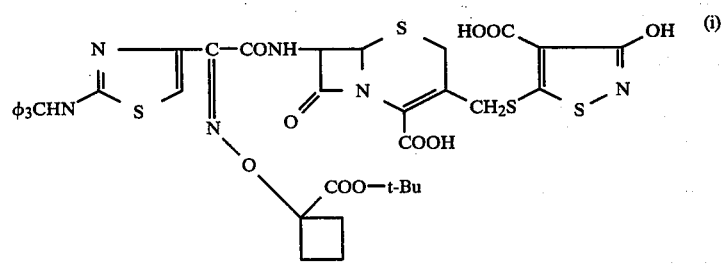

By treating 1.8 g of (Z)-α-(1-tert-butoxycarbonylcyclopent-1-yloxyimino)-2-(2-tritylaminothiazol-4-yl)acetic acid, 18 ml of dioxane, 405 mg of 1-hydroxybenztriazole, and 740 mg of dicyclohexylcarbodiimide as in Example 10-(i), a dioxane solution of an active ester was obtained. On the other hand, an aqueous solution was prepared using 1.2 g of 7-amino-3-[(4-carboxy-3-hydroxyisothiazol-5-yl)thiomethyl]-Δ³-cephem-4-carboxylic acid, 10 ml of water, and 518 mg of sodium hydrogencarbonate and after adding dropwise the aforesaid dioxane solution of the active ester to the aqueous solution, the mixture was treated as in Example 10-(i) to provide 475 mg of (Z)-3-[(4-carboxy-3-hydroxyisothiazol-5-yl)-thiomethyl]-7-[α-(1-tert-butoxycarbonylcycloopent-1-yloxyimino)-α-(2-tritylaminothiazol-4-yl)acetamido]-Δ³-cephem-4-carboxylic acid.

Infrared absorption spectra:
$\nu_{max}^{KBr}$ cm$^{-1}$: 3350, 3200, 2940, 1775, 1710, 1670, 1480–1520, 1440, 1365, 1245, 1150, 990, 750, 695.

Nuclear magnetic resonance spectra (in d$_6$-DMSO) δ(ppm): 1.34 (9H, s, —t—Bu) 2.64 (4H, m, cyclopentane ring) 2.95 (4H, m, cyclopentane ring) 3.62 (2H, q, CH$_2$— at 2-position) 4.16 (2H, q, —CH$_2$S—) 5.14 (1H, d, CH at 6-position) 5.68 (1H, q, CH at 7-position) 6.64 (1H, s,

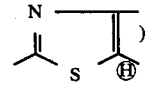

7.1–7.4 (15H, 3φ) 8.74 (1H, s, —NH—) 9.23 (1H, d, —CONH—)

By treating 475 mg of the aforesaid compound as in Example 10-(ii), 310 mg of (Z)-7-[α-(2-aminothiazol-4-yl)-α-(1-carboxycyclopent-1-yloxyimino)acetamido]-3-[(4-carboxy-3-hydroxyisothiazol-5-yl)thiomethyl]-Δ³-cephem-4-carboxylic acid was obtained. The product was dissolved in a mixture of 5 ml of water and 78 mg of sodium hydrogencaronate and after filtering away insoluble materials, the solution was applied to a column containing an ion-exchange resin, Diaion HP-20. The product was eluted using first water and then 20% methanol. The fractions containing the desired product were collected, concentrated, and the residue was liophilized to provide 300 mg of tris-sodium (Z)-7-[α-(2-aminothiazol-4-yl)-α-(1-carboxylatocyclopent-1-yloxyimino)acetamido]-3-[(α-carboxylato-3-hydroxyisothiazol-5-yl)thiomethyl]-Δ³-cephem-4-carboxylate.

Infrared absorption spectra: $\nu_{max}^{KBr}$ cm$^{-1}$: 3380–3400, 1755, 1590, 1520, 1380

Nuclear magnetic resonance spectra (in D$_2$O) δ(ppm): 1.70 (4H, m, cyclopentane ring) 2.06 (4H, m, cyclopentane ring) 3.62 (2H, q, CH$_2$ at 2-position) 5.18 (1H, d, CH at 6-position) 5.76 (1H, d, CH at 7-position) 6.95 (1H, s,

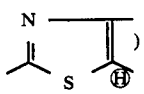

EXAMPLE 13

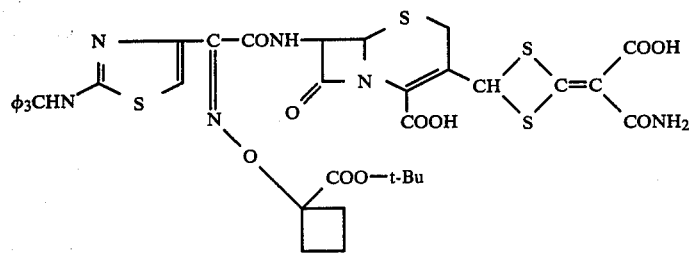

By following the same procedure as in Example 11-(i) *using (Z)-α-(1-t-butoxycarbonylcyclopent-1-yloxyimino)-2-(2-tritylaminothiazol-4-yl)acetic acid and 7-amino-3-[(4-carboxy-3-hydroxyisothiazol-5-yl)thiomethyl]-Δ³-cephem-4-carboxylic acid, (Z)-3-[4-(1-carbamoyl-1-carboxymethylene)-1,3-dithiethane-2-yl]-7-[α-(1-tert-butoxycarbonylcyclopent-1-cycloxyimino)-2-(2-tritylaminothiazol-4-yl)acetamido]-Δ³-cephem-4-carboxylic acid was obtained.

Infrared absorption spectra: $\nu_{max}^{KBr}$ cm$^{-1}$: 3350, 2950, 1770, 1670, 1490, 1360, 1250, 1150, 990, 690

Nuclear magnetic resonance spectra (in d$_6$-DMSO): δ(ppm): 1.36 (9H, s, —t—Bu) 1.66, 1.96 (each 4H, m, cyclopentane ring) 3.92 (2H, s, CH$_2$ at 2-position) 5.15 (1H, d, CH at 6-position) 5.72 (1H, s,

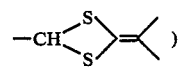

5.7–5.8 (1H, q, CH at 7-position) 6.66 (1H, s,

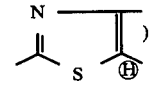

7.1–7.4 (15H, Cφ$_3$) 8.74 (1H, s, φ$_3$C<u>H</u>N—) 9.2–9.36 (1H, d, —CONH—)

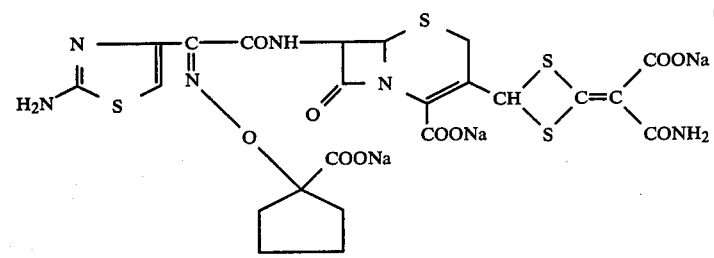

By following the same procedure as in Example 11-(ii) using (Z)-3-[4-(1-carbamoyl-1-carboxymethylidene)-1,3-dithiethane-2-yl]-7-[α-(1-tert-butoxycarbonylcyclopent-1-yloxyimino)-2-(2-tritylaminothiazol-4-yl)acetamido]-Δ³-cephem-4-carboxylic acid, 206 mg of (Z)-7-[α-(2-aminothiazol-4-yl)-α-(1-carboxycyclopent-1-yloxyimino) acetamido]-3-[4-(1-carbamoyl-1-carboxymethylene)1,3-dithiethane-2-yl]-Δ³-cephem-4-carboxylic acid was obtained. The product was passed through an ion-exchange resin, Diaion HP-20 and then lyophilized to provide tris-sodium (Z)-7-[α-(2-aminothiazol-4-yl)-α-(1-carboxylatocyclopent-1-yloxyimino)acetamido]-3-[4-(1-carbamoyl-1-carbox-ylatomethylene)-1,3-dithiethane-2-yl]-Δ³-cephem-4-carboxylate.

Infrared absorption spectra $\nu_{max}^{KBr}$ cm$^{-1}$: 3350–3400, 1750, 1620, 1520, 1380, 1350

Nuclear magnetic resonance spectra (in D$_2$O): δ(ppm): 1.73, 2.06 (each 4H, m, cyclopentane ring) 4.06 (2H, d, CH$_2$ at 2-position) 5.28 (1H, d, CH at 6-position) 5.69 (1H, s, (i)

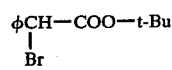

5.84 (1H, d, CH at 7-position) 7.00 (1H, s,

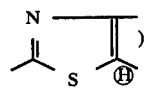

REFERENCE EXAMPLE 6

φCH—COO—t-Bu (i)
|
Br

In a closed tube was placed about 40 ml of isobutene, 25 g of α-bromophenylacetic acid, 1 ml of concentrated sulfuric acid, and 10 ml of dry ethyl ether and the a mixture was allowed to stand overnight in the closed tube at room temperature. After the reaction was over, the reaction mixture was poured into a mixture of 150 ml of ice water and 10 g of sodium hydrogencarbonate and then extracted with 200 ml and then 100 ml of ether. The organic layers were collected, washed twice each time with 50 ml of water and once with 50 ml of a saturated aqueous sodium chloride solution, and dried by anhydrous magnesium sulfate. By distilling off ether from the reaction mixture, 31.6 g of the desired product was obtained.

Infrared absorption spectra: $\nu_{max}^{KBr}$ cm$^{-1}$: 2960, 1730, 1360, 1220, 1150, 1130, 740, 690.

Nuclear magnetic resonance spectra (in CDCl₃):
δ(ppm): 1.40 (9H, s, —t—Bu) 5.25 (1H, s, —CH—) 7.1–7.7 (5H, φ)

In 100 ml of methylene dichloride was suspended 4.29 g of 2-hydroxyimino-2-(2-tritylaminothiazol-4-yl)acetic acid and after adding slowly 3 g of diphenyldiazomethane, the mixture was allowed to stand for 4 hours at room temperature.

After the reaction was over, methylene dichlororide was distilled off to provide a caramel material. The caramel material was subjected to silica gel column chromatography, eluted with a mixture of n-hexane and ethyl acetate (3:1), and the fractions containing the desired products were collected and concentrated to provide 5.3 g of white crystals having a melting point of 170°–171° C.

Infrared absorption spectra: $\nu_{max}^{KBr}$ cm⁻¹: 3330, 3030, 2750, 1725, 1530, 1490, 1280, 1155, 990, 690

Nuclear magnetic resonance spectra (in CDCl₃):
δ(ppm): 6.25 (1H, s,

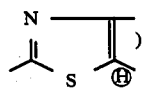

7.11 (1H, s, —CHφ₂) 7.2–7.5 (25H, 5φ)

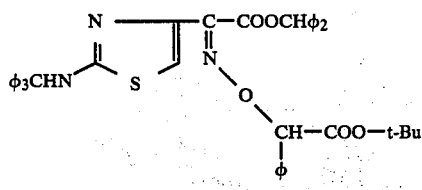

In 20 ml of dimethyl sulfoxide was dissolved 2.97 g (0.005 mole) of benzhydryl (Z)-2-hydroxyimino-2-(2-tritylaminothiazol-4-yl)acetate and after adding thereto 0.68 g (0.005 mole) of powdered potassium carbonate and 1.56 g (0.0057 mole) of tert-butyl-α-bromophenyl acetate, the reaction was allowed to stand overnight at room temperature. After the reaction was over, the reaction mixture was dispersed in 200 ml of ice water and extracted with 100 ml and then 50 ml of ethyl acetate. The organic layers were collected, washed twice each time with 30 ml of water and then with 30 ml of a saturated aqueous sodium chloride solution, dried with anhydrous magnesium sulfate, and the solvent was distilled off under reduced pressure to provide a caramel material. The caramel material was dissolved in 1 ml of ethyl acetate and powdered by the addition of 100 ml of n-hexane. The powder was recovered by filtration and dried to provide 3.04 g (yield of 77.4%) of benzhydryl (Z)-2-(α-tert-butoxycarbonylbenzyloxyimino)-2-(2-tritylaminothiazol-4-yl)acetate.

Infrared absorption spectra: $\nu_{max}^{KBr}$ cm⁻¹: 1740, 1730, 1530, 1155, 1140, 1020, 735, 690

Nuclear magnetic resonance spectra (in CDCl₃):
δ(ppm): 1.39 (9H, s, —t—Bu) 5.71 (1H, s

6.27 (1H, s,

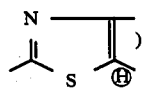

6.83 (1H, s, —HN—) 7.08 (1H, s, —CHφ₂) 7.1–7.5 (25H, 5φ)

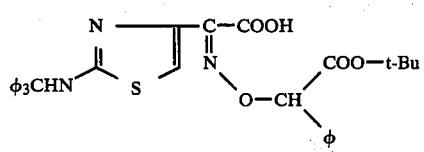

To a mixture of 4 ml of methylene dichloride and 1 ml of anisole was added 2.61 g (0.0033 mole) of benzhydryl (Z)-2-(α-tert-butoxycarbonylbenzyloximino)-2-(2-tritylaminothiazol-4-yl)acetate and after cooling the mixture to −30° C., 3 ml of trifluoroacetic acid was added dropwise to the mixture at a temperature below −20° C. over a period of 5 minutes. Thereafter, the mixture was maintained for one hour at −20° C. to −15° C. and then, methylene dichloride and trifluoroacetic acid were distilled off at low temperature under reduced pressure to provide an oily product. The oily product was subjected to silica gel column chromatography, eluted with a mixture of chloroform, isopropyl alcohol, and formic acid (90:10:2), the fractions containing the desired product were collected, and the solvents were distilled off to provide 1.15 g (Z)-(α-tert-butoxycarbonylbenzyloximino)-2-(2-tritylaminothiazol-4-yl)acetic acid.

Infrared absorption spectra: $\nu_{max}^{KBr}$ cm⁻¹: 2970, 2920, 1740, 1590, 1570, 1440, 1360, 1190, 1150, 690.

Nuclear magnetic resonance spectra (in d₆-DMSO):
δ(ppm): 1.35 (9H, s, —t—Bu) 5.48 (1H, s,

6.86 (1H, s,

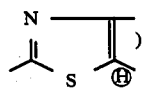

7.28 (15H, 3φ) 7.38 (5H, 1φ)

EXAMPLE 14

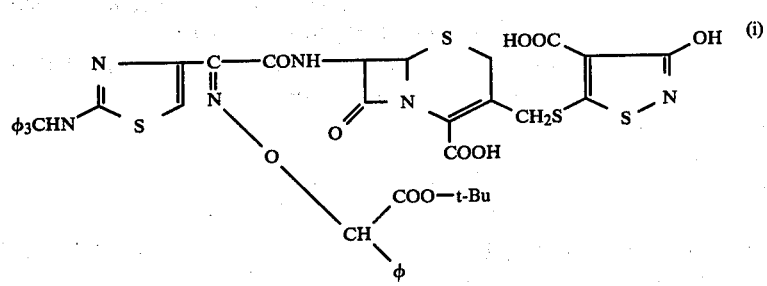

By following the same procedure as in Example 10-(i) using (Z)-(α-tert-butoxycarbonylbenzyloxyimino)-2-(2-tritylaminothiazol-4-yl)acetic acid and 7-amino-3-[(4-carboxy-3-hydroxyisothiazol-5-yl)thiomethyl]-$\Delta^3$-cephem-4-carboxylic acid, the desired product was obtained.

Infrared absorption spectra: $\nu_{max}^{KBr}$ cm$^{-1}$: 2960, 1780, 1720, 1680, 1520, 1490, 1150, 750 695

Nuclear magnetic resonance spectra (in d$_6$-DMSO): δ(ppm): 1.35 (9H, s, —t—Bu) 5.44 (1H, s, $$-\overset{|}{\underset{|}{C}}H-)$$

6.73, 6.76 (1H, s(each)),

7.25 (15H, 3φ)
7.38 (5H, φ)

—CH$_2$—) 5.14, 5.18 (1H, d(each), CH at 6-position) 5.57 (1H, s, $$-\overset{|}{\underset{|}{C}}H-)$$

6.78, 6.83 (1H, s(each)),

9.50, 9.60 (1H, d(each), —NHCO—)

EXAMPLE 15

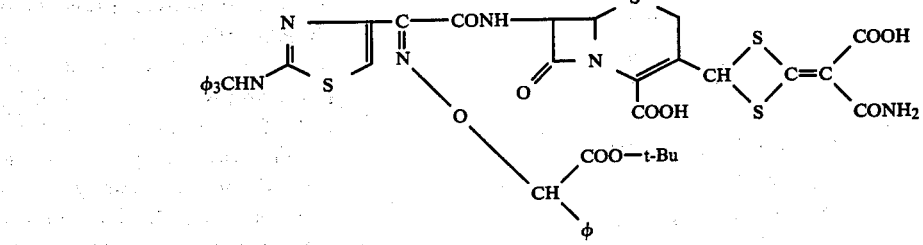

By following the same procedure as in Example 5-(i) using (Z)-3-[(4-carboxy-3-hydroxyisothiazol-5-yl)thiomethyl]-7-[α-(2-tributylaminothiazol-4-yl)-α-(1-tert-butoxycarbonylbenzyloxyimino)acetoamido]-$\Delta^3$-cephem-4-carboxylic acid, the desired product was obtained.

Infrared absorption spectra: $\nu_{max}^{KBr}$ cm$^{-1}$: 3350,

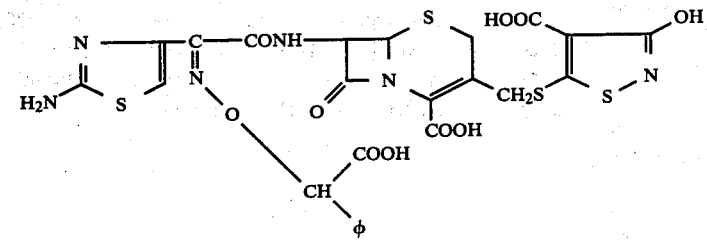

By following the same procedure as in Example 10-(ii) using (Z)-3-[(4-carboxy-3-hydroxyisothiazol-5-yl)thiomethyl]-7-[α-(2-tritylaminothiazol-4-yl)-α-(1-tert-butoxycarbonylbenzyloxyimino)acetamido]-$\Delta^3$-cephem-4-carboxylic acid, the desired product was obtained.

Infrared absorption spectra: $\nu_{max}^{KBr}$ cm$^{-1}$: 3000–3400, 1770, 1670, 1620, 1350, 1240, 1250

Nuclear magnetic resonance spectra (in d$_6$-DMSO): δ(ppm): 3.54 (2H, q, CH$_2$ at 2-position) 4.18 (2H, q, 2960, 1780, 1670, 1490, 1365, 1250, 1150, 750, 690, Nuclear magnetic resonance spectra (in d$_6$-DMSO): δ(ppm): 1.34 (9H, s, —t—Bu) 3.86 (2H, CH$_2$ at 2-position) 5.10 (1H, d, CH at 6-position) 5,24 (1H, s,

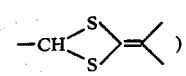

5.73 (1H, CH at 7-position) 6.74 (1H,

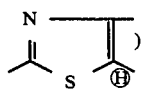)

7.1–7.5 (20H, 4φ) 8.82 (1H, s, —NH—) 9.44 (1H, d,d, —CONH—)

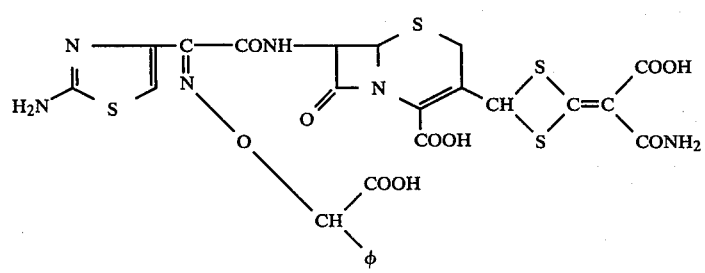

In 4 ml of formic acid was dissolved 100 mg of the desired product in Example 15-(i) and the mixture was allowed to stand overnight at room temperature. Then, after adding thereto 4 ml of water, the mixture was reacted for 90 minutes at 50°–55° C. After the reaction was over, formic acid and water were distilled off under reduced pressure and the residue was dissolved in 10 ml of ethyl alcohol. Then, ethanol was partially distilled off to provide an oily product, which was powdered by the addition of 50 ml of a mixture of ether and n-hexane (1:1) to provide 65 mg of the desired product.

Infrared absorption spectra: $\nu_{max}^{KBr}$ cm$^{-1}$: 2900–3400, 1775, 1670, 1625, 1190, 1135, 715

Nuclear magentic resonance spectra (in d$_6$-DMSO): δ(ppm): 3.92 (2H, s, CH$_2$ at 2-position) 5.14, 5.18 (1H, d(each), CH at 6-position) 5.58 (1H, s,

5.75, 5.78 (1H, s(each),

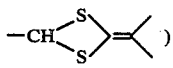)

5.86 (1H, q, CH at 7-position) 6.82, 6.86 (1H, s(each),

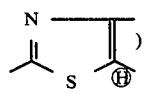)

7.3–7.6 (5H, φ)

REFERENCE EXAMPLE 7

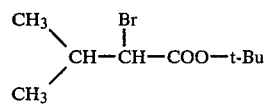 (i)

By following the same procedure as in Reference example 6-(i) using α-bromoisovaleric acid, the desired product was obtained.

Infrared absorption spectra: $\nu_{max}^{KBr}$ cm$^{-1}$: 2970, 1730, 1365, 1135

Nuclear magnetic resonance spectra (in d$_6$-DMSO): δ(ppm): 1.00 (3H, d, CH$_3$—) 1.05 (3H, d, CH$_3$—) 1.45 (9H, s, —t—Bu) 1.6–2.5 (1H, m,

3.88 (1H, d,

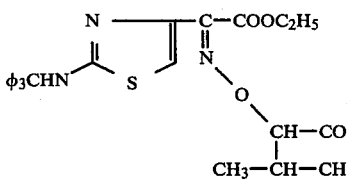 (ii)

By following the same procedure as in Reference example 6-(iii) using ethyl(Z)-2-hydroxyimino-2-(2-tritylaminothiazol-4-yl)acetate hydrochloride and tert-butyl-α-bromoisovalerate, the desired product was obtained.

Melting point: 109°–110° C.

Infrared absorption spectra: $\nu_{max}^{KBr}$ cm$^{-1}$: 3250, 2960, 1730, 1330, 1290, 1180, 1020, 695

Nuclear magnetic resonance spectra (in CDCl$_3$): δ(ppm): 0.99 (3H, t, CH$_3$—) 1.32 (3H, d, CH$_3$—) 1.45 (12H, s, —t—Bu, CH$_3$—) 2.0–2.4 (1H, m,

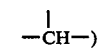

4.38 (2H, q, —CH$_2$—) 4.56 (1H, d,

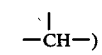

6.54 (1H, s,

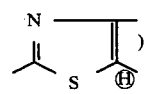)

6.91 (1H, d, —NH—) 7.1–7.5 (15H, 3φ)

7.1–7.3 (15H, 3φ) 8.78 (1H, s, —NH—)

EXAMPLE 16

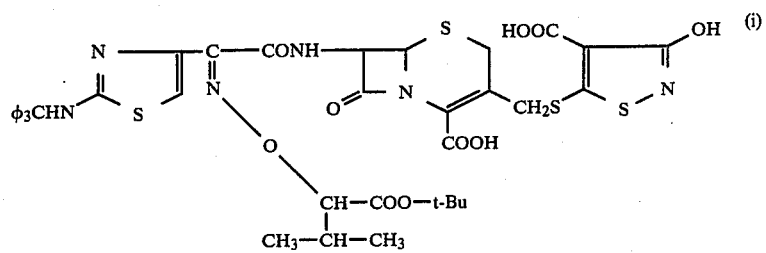

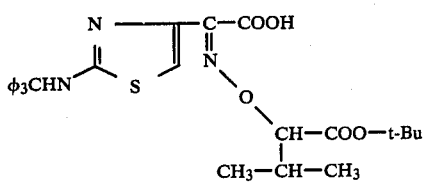

In 343 ml of methanol was dissolved 6.13 g (0.01 mole) of the desired product in Reference example 7-(ii) and then after adding thereto a solution of 3.17 g (0.0225 mole) of potassium carbonate dissolved in 38 ml of water, the mixture was reacted for 4 hours under refluxing. After the reaction was over, methanol was distilled off and the aqueous solution thus formed was mixed with 100 ml of water, 50 ml of 2N hydrochloric acid and extracted with 200 ml and then 100 ml of ethyl acetate. The organic layers were collected, washed twice each time with 50 ml of water and then with 50 ml of a saturated aqueous sodium chloride solution, dried with anhydrous magnesium sulfate, and ethyl acetate was distilled off under reduced pressure to provide 4.37 g of the desired product.

By following the same procedure as in Example 10-(i) using (Z)-2-(1-tert-butoxycarbonyl-2-methylpropoxyimino)-2-(2-tritylaminothiazol-4-yl)acetic acid and 7-amino-3-[(4-carboxy-3-hydroxyisothiazol-5-yl)thiomethyl]-Δ$^3$-cephem-4-carboxylic acid, the desired product was obtained.

Infrared absorption spectra: $\nu_{max}^{KBr}$ cm$^{-1}$: 3440–3480, 2950, 1775, 1710, 1670, 1480–1520, 1360, 1150, 690

Nuclear magnetic resonance spectra (in d$_6$-DMSO): δ(ppm): 0.94 (3H, d, CH$_3$—) 1.40 (9H, s, t—Bu) 3.64 (2H, q, —CH$_2$—) 4.14 (2H, q, —CH$_2$—) 5.15 (1H, d, CH at 6-position) 5.6–5.8 (1H, m, CH at 7-position) 6.67, 6.70 (1H, s(each),

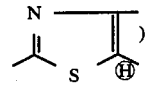

7.1–7.5 (15H, 3φ) 8.76 (1h, s, —NH—) 9.40 (1H, m, —CONH—)

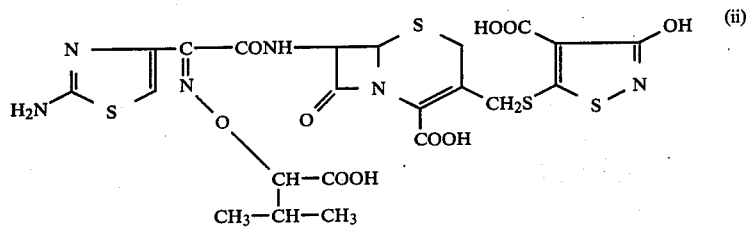

Infrared absorption spectra: $\nu_{max}^{KBr}$ cm$^{-1}$: 3380, 3230, 2960, 1735, 1695, 1530, 1155, 1135, 1030, 690

Nuclear magnetic resonance spectra (in d$_6$-DMSO) δ(ppm): 0.92 (6H, d, CH$_3$—) 1.40 (9H, s, —t—Bu) 1.8–2.2 (1H, m,

|
—CH—)

4.17 (1H, d,

|
—CH—)

6.82 (1H, s,

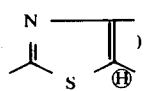

By following the same procedure as in Example 10-(ii) using (Z)-3-[(4-carboxy-3-hydroxyisothiazol-5-yl)thiomethyl]-7-[α-(2-tritylaminothiazol-4-yl)-α-(1-tert-butoxycarbonyl-2-methylpropoxyimino)acetamido]-Δ$^3$-cephem-4-carboxylic acid, the desired product was obtained.

Infrared absorption spectra: $\nu_{max}^{KBr}$ cm$^{-1}$: 3300—3370, 2960, 1770, 1690–1720, 1670, 1625 1020

Nuclear magnetic resonance spectra (in d$_6$-DMSO): δ(ppm): 0.95 (6H, d, CH$_3$—) 3.66 (2H, q, CH$_2$ at 2-position) 4.19 (2H, q, —CH$_2$—) 5.19 (1H, d, CH at 6-position) 5.68–5.9 (1H, m, CH at 7-position) 6.72, 6.76 (1H, s(each),

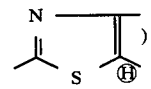

9.41, 9.50 (1H, d(each), —CONH—)

EXAMPLE 17

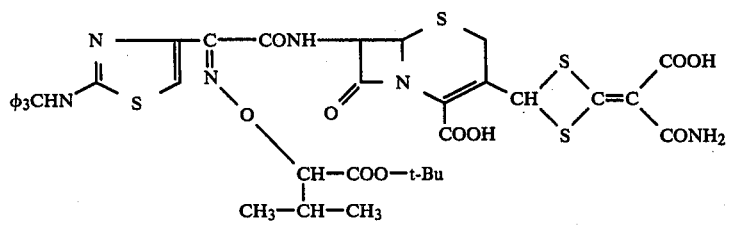

By following the same procedure as in Example 5-(i) using the same starting compound as in Example 16 (ii), the desired product was obtained.

Infrared absorption spectra: $\nu_{max}^{KBr}$ cm$^{-1}$: 3350, 2960, 1780, 1670, 1490, 1360, 1250, 1150, 1020, 690

Nuclear magnetic resonance spectra (in d$_6$-DMSO): δ(ppm): 0.94 (6H, d, CH$_3$—) 1.40 (9H, s, —t—Bu) 1.9–2.2 (1H, m,

3.90 (2H, q, CH$_2$ at 2-position) 4.18 (1H, d, —CH—) 5.14 (1H, d, CH at 6-position) 5.73 (1H, s,

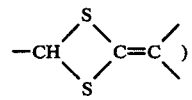

5.6–5.86 (1H, m, CH at 7-position) 6.72 (1H, s,

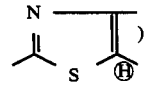

7.1–7.5 (15H, 3φ) 8.76 (1H, s, —NH—) 9.3–9.54 (1H, m, —CONH—)

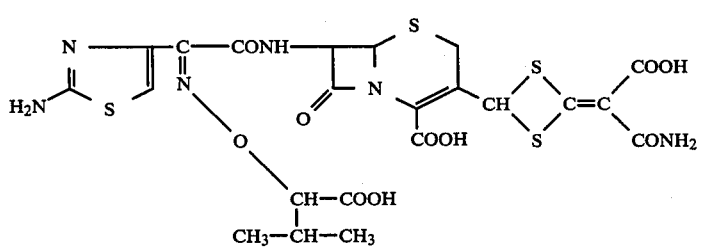

By following the same procedure as in Example 15-(ii) i.e. removing the protective group of (Z)-3-[4-(carbamoylcarboxymethylene)-1,3-dithietan-2-yl]-7-[α-(2-tritylaminothiazol-4-yl)-α-(1-tert-butoxycarbonyl-2-methylpropoxyimino)acetamido]-Δ$^3$-cephem-4-carboxylic acid with formic acid, the desired product was obtained.

Infrared absorption spectra: $\nu_{max}^{KBr}$ cm$^{-1}$: 3100–3400, 2960, 1770, 1620, 1520, 1380, 1230–1270, 1020

Nuclear magnetic resonance spectra (in d$_6$-DMSO): δ(ppm): 0.97 (6H, d, CH$_3$—) 1.9–2.3 (1H, m, —CH—) 3.93 (2H, q, CH$_2$ at 2-position) 4.22, 4.28 (1H, d(each),

5.18 (1H, d, CH at 6-position) 5.66 (1H, s,

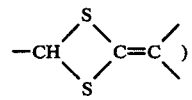

5.8–5.98 (1H, m, CH at 7-position) 6.73, 6.78 (1H, s(each),

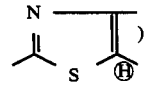

7.23 (1H, s, —NH—) 9.38–9.64 (1H, m, —CONH—)

REFERENCE EXAMPLE 8

BrCH—COO—t-Bu (i)
|
CH$_3$

By following the same procedure as in Reference example 6-(i) using α-bromopropionic acid, the desired product was obtained.

(ii)

Infrared absorption spectra: $\nu_{max}^{KBr}$ cm$^{-1}$: 2960, 1730, 1365, 1230, 1145, 840

Nuclear magnetic resonance spectra (in CDCl$_3$) δ(ppm): 1.48 (9H, s, —t—Bu) 1.77 (3H, d, CH$_3$—) 4.28 (1H, q,

(ii) [Structure: φ3CHN-thiazole-C(=N-O-CH(CH3)-COO-t-Bu)-COOEt]

By following the same procedure as in Reference example 6-(iii) using ethyl (Z)-2-hydroxyimino-2-(2-tritylaminothiazol-4-yl)acetate hydrochloride and tert-butyl-α-bromopropionate, the desired product was obtained.

Melting point: 58°–59° C.

Infrared absorption spectra: $\nu_{max}^{KBr}$ cm$^{-1}$: 3330–3380, 2970, 1730, 1525, 1270, 1180 1155, 1030, 970, 690

Nuclear magnetic resonance spectra (in CDCl$_3$):
δ(ppm): 1.36 (3H, t, CH$_3$—) 1.25 (9H, s, —t—Bu) 1.57 (3H, d, CH$_3$—) 4.38 (2H, q, —CH$_2$—) 4.80 (1H, q,

|
—CH—)

6.52 (1H, s

[thiazole structure]

6.88 (1H, s, —NH—) 7.1–7.5 (15H, s, 3φ)

(iii) [Structure: φ3CHN-thiazole-C(=N-O-CH(CH3)-COO-t-Bu)-COOH]

By following the same procedure as in Reference example 7-(iii) using Ethyl(Z)-2-(1-tert-butoxycarbonyl-ethoxyimino)-2-(2-tritylaminothiazol-4-yl)acetate, the desired product was obtained.

Melting point: 166°–167° C. (decomposed)
Infrared absorption spectra:

$\nu_{max}^{KBr}$ cm$^{-1}$: 3250, 2960, 1710, 1530, 1245, 1155, 1035, 835, 690

Nuclear magnetic resonance spectra (in d$_6$-DMSO):
δ(ppm): 1.33 (3H, d, CH$_3$—) 1.38 (9H, s, —t—Bu) 4.52 (1H, q,

|
—CH—)

6.80 (1H, s,

[thiazole structure]

7.1–7.5 (15H, 3φ) 8.76 (1H, s, —NH—)

EXAMPLE 18

(i) [Complex cephem structure with φ3CHN-thiazole, oxime-O-CH(CH3)-COO-t-Bu, CONH, β-lactam, CH2S-isothiazole(HOOC, OH)]

By following the same procedure as in Example 10-(i) using (Z)-2-(1-tert-butoxycarbonyl-ethoxyimino)-2-(2-tritylaminothiazol-4-yl)acetic acid and 7-amino-3-[(4-carboxy-3-hydroxyisothiazol-5-yl)thiomethyl]-Δ$^3$-cephem-4-carboxylic acid, the desired product was obtained.

Infrared absorption spectra: $\nu_{max}^{KBr}$ cm$^{-1}$: 2920, 1780, 1720, 1670, 1520, 1440, 1360, 1150, 750, 690

Nuclear magnetic resonance spectra (in d$_6$-DMSO):
δ(ppm): 1.27 (3H, d, CH$_3$—) 1.39 (9H, s, t—Bu) 3.63 (2H, q, CH$_2$ at 2-position) 4.18 (2H, q, —CH$_2$—) 4.49 (1H, q,

|
—CH—)

5.15 (1H, d, CH at 6-position) 5.64–5.80 (1H, m, CH at 7-position) 6.72 (1H, s,

[thiazole structure]

7.1–7.5 (15H, 3φ) 8.80 (1H, s, —NH—) 9.38, 9.41 (1H, d(each), —CONH—)

(ii) [Complex cephem structure with H2N-thiazole, oxime-O-CH(CH3)-COOH, CONH, β-lactam, CH2S-isothiazole(HOOC, OH)]

By following the same procedure as in Example 10-(ii) using (Z)-3-[(4-carboxy-3-hydroxyisothiazol-5-yl)thiomethyl]-7-[α-(2-tritylaminothiazol-4-yl)-α-(1-tert-butoxycarbonyl-ethoxyimino)acetamido]-Δ³-cephem-4-carboxylic acid, the desired product was obtained.

Infrared absorption spectra: $\nu_{max}^{KBr}$ cm$^{-1}$: 2900–3300, 1760, 1690–1720, 1670, 1620, 1185, 1130, 1030

Nuclear magnetic resonance spectra (in d$_6$-DMSO): δ(ppm): 1.40 (3H, d, CH$_3$—) 3.69 (2H, q, CH$_2$ at 2-position) 4.20 (2h, q, —CH$_2$—) 4.66 (1H, q,

5.22 (1H, d, CH at 6-position) 5.83, 5.89 (1H, d(each), CH at 7-position) 6.72, 6.80 (1H, s(each),

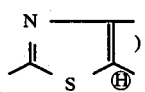

9.44, 9.48 (1H, d(each), —CONH—)

EXAMPLE 19

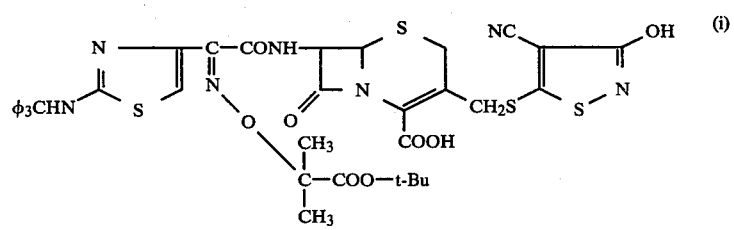

To 15 ml of dioxane were added 1.7 g (0.003 mole) of (Z)-α-(1-tert-butoxycarbonyl-1-methylethoxyimino)-α-(2-tritylaminothiazol-4-yl)acetic acid, 0.4 g (0.003 mole) of 1-hydroxybenzotriazole, and 0.62 g (0.003 mole) of dicyclohexylcarbodiimide and the mixture was stirred for one hour at room temperature. The reaction mixture was filtered to remove dicyclohexylurea precipitated. The filtrate was added dropwise to a mixture of 1.1 g (0.003 mole) of 7-amino-3-[(3-hydroxy-4-cyanoisothiazol-5-yl)thiomethyl]-Δ³-cephem-4-carboxylic acid, 1.0 g (0.012 mole) of sodium hydrogencarbonate, and 15 ml of water. Then, after adding thereto 15 ml of dioxane, the resultant mixture was stirred overnight at room temperature. To the reaction mixture was added 50 ml of water and insoluble materials formed were filtered off. On the filtrate was placed a layer of 100 ml of ethyl acetate and the pH thereof was adjusted to 2 by 2N hydrochloric acid with stirring under ice-cooling. The ethyl acetate layer formed was recovered, washed three times each time with 100 ml of water, dried with anhydrous magnesium sulfate, and concentrated under reduced pressure to provide 1.2 g of the powder of crude 3-[(3-hydroxy-4-cyanoisothiazol-5-yl)thiomethyl]-7-[α-(1-tert-butoxycarbonyl-1-methylethoxyimino)-α-(2-tritylaminothiazol-4-yl)acetamido]-Δ³-cephem-4-carboxylic acid.

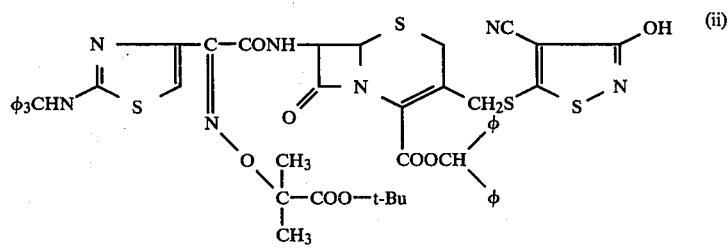

In 20 ml of methylene dichloride was dissolved 1.2 g of the compound obtained in the aforesaid process and after adding thereto 0.2 g of diphenyldiazomethane, the mixture was stirred for one hour at room temperature. The reaction mixture was concentrated. The residue was subjected to silica gel column chromatography, eluted with a mixture of benzene and ethyl acetate (8:2), and the fractions containing the desired product were collected and concentrated to provide 310 mg of (Z)-3-[(3-hydroxy-4-cyanoisothiazol-5-yl)thiomethyl]-7-[α-(1-tert-butoxycarbonyl-1-methylethoxyimino)-α-(2-tritylaminothiazol-4-yl)acetamido]-Δ³-cephem-4-carboxylic acid benzhydryl ester.

Infrared absorption spectra: $\nu_{max}^{KBr}$ cm$^{-1}$: 2210, 1775, 1710, 1675

Nuclear magnetic resonance spectra (in CDCl$_3$-CD$_3$OD): δ(ppm): 1.38 (6H, s) 1.58 (9H, s) 3.47 (2H, q) 4.07 (2H, q) 5.55 (1H, d) 5.90 (1H, d) 6.70 (1H, s) 6.85 (1H, s)

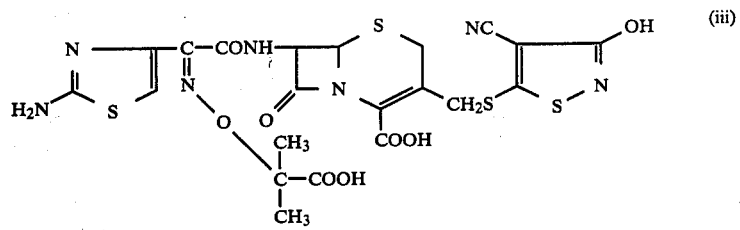 (iii)

To 310 mg of the compound obtained in the above process were added 0.5 ml of anisole and 1 ml of trifluoroacetic acid under ice-cooling, and the mixture was stirred for 30 minutes at room temperature. The reaction mixture was ice-cooled and after adding thereto 0.3 ml of water, the mixture was further stirred for 2 hours.

The reaction mixture was concentrated under reduced pressure and treated with ether to form a powder. The powder was recovered by filtration, washed with ether, and dried under reduced pressure to provide 130 mg of (Z)-3-[(3-hydroxy-4-cyanoisothiazol-5-yl)thiomethyl]7-[α-(2-aminothiazol-4-yl)-α-(1-carboxy-1-methylethoxyimino)acetamido]-Δ³-cephem-4-carboxylic acid.

Infrared absorption spectra: $\nu_{max}^{KBr}$ cm$^{-1}$: 2210, 1770, 1670

Nuclear magnetic resonance spectra (in d$_6$-DMSO): δ(ppm): 2.40 (6H, s) 3.66 (2H, q) 4.30 (2H, q) 5.18 (1H, d) 5.82 (1H, q) 6.70 (1H, s) 9.35 (1H, d)

EXAMPLE 20

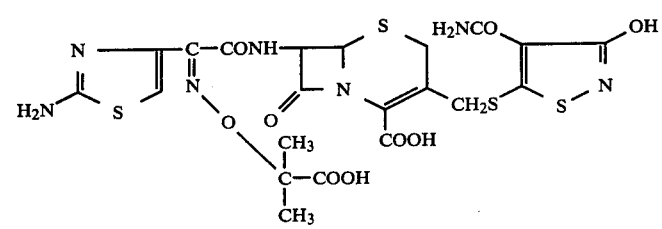

By following the same procedure as in Example 19 using (Z)-α-(1-tert-butoxycarbonyl-1-methylethoxyimino)-α-(2-tritylaminothiazol-4-yl)acetic acid and 7-amino-3-[(3-hydroxy-4-carbamoylisothiazol-5-yl)thiomethyl]-Δ³-cephem-4-carboxylic acid, the desired product was obtained.

Infrared absorption spectrum: $\nu_{max}^{KBr}$ cm$^{-1}$: 1770

Nuclear magnetic resonance spectra (in d$_6$-DMSO): δ(ppm): 1.43 (6H, s) 3.65 (2H, q) 4.07 (2H, q) 5.18 (1H, d) 5.83 (1H, q) 7.72 (1H, s) 9.36 (1H, d)

EXAMPLE 21

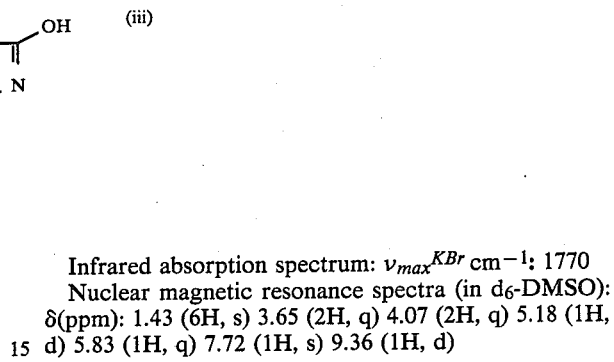

By following the same procedure as in Example 19 using (Z)-α-(1-tert-butoxycarbonyl-1-methylethoxyimino)-α-(2-tritylaminothiazol-4-yl)acetic acid and 7-amino-3-[(3-hydroxy-4-N,N-dimethylcarbamoylisothiazol-5-yl)thiomethyl]-Δ³-cephem-4-carboxylic acid, the desired product was obtained.

Infrared absorption spectrum: $\nu_{max}^{KBr}$ cm$^{-1}$: 1770

Nuclear magnetic resonance spectra (d$_6$-DMSO): δ(ppm): 1.43 (6H, s) 2.87 (6H, s) 3.60 (2H, q) 4.12 (2H, q) 5.17 (1H, d) 5.77 (1H, q) 6.68 (1H, s) 9.32 (1H, d)

EXAMPLE 22

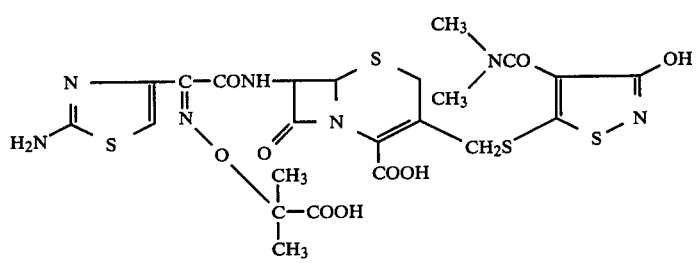 (i)

By following the same procedure as in Example 19-(i) using (Z)-α-(2-bromoethoxyimino)-α-(2-tritylaminothiazol-4-yl)acetic acid and 7-amino-3-[(3-hydroxy-4-carboxyisothiazol-5-yl)thiomethyl]-Δ³-cephem-4-carboxylic acid, the desired product was produded.

Infrared absorption spectrum: $\nu_{max}^{KBr}$ cm$^{-1}$: 1755

Nuclear magnetic resonance spectra (in d₆-DMSO): δ(ppm): 3.5-3.7 (4H, m), 4.1-4.4 (4H, m), 5.15 (1H, d), 5.72 (1H, q), 6.77 (1H, s), 8.27 (15H, m)

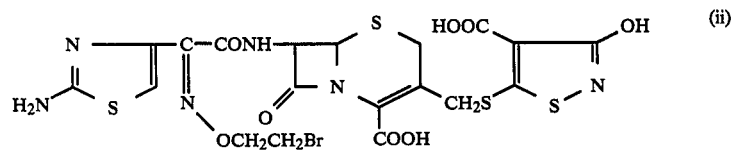

By treating the aforesaid compound according to the process of Example 19-(iii), the desired product was obtained.

Infrared absorption spectra: $\nu_{max}^{KBr}$ cm$^{-1}$: 1770, 1650 solution, dried with anhydrous magnesium sulfate and concentrated under reduced pressure. The residue thus formed was subjected to silica gel column chromatography, eluted with a mixture of chloroform, methanol, and formic acid (80:20:2 in volume ratio), the fractions containing the desired product were collected, and the solvents were distilled off to provide 130 mg of the desired product.

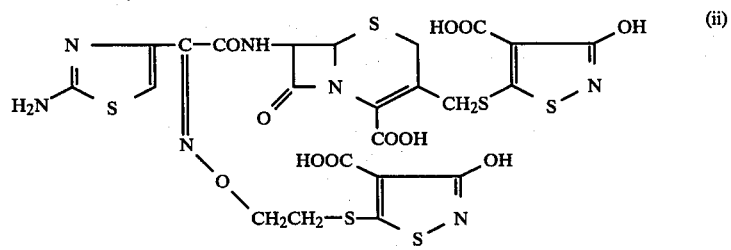

Nuclear magnetic resonance spectra (in d₆-DMSO) δ(ppm): 3.5-3.8 (4H, m) 4.0-4.5 (4H, m) 5.17 (1H, d) 5.77 (1H, q) 6.76 (1H, s).

EXAMPLE 23

To 130 ml of the trityl compound obtained in the above process was added 2 ml of trifluoroacetic acid and 1.5 ml of water and the mixture was reacted for 2 hours at 15°-20° C. The reaction mixture was concentrated under reduced pressure and the residue was pow-

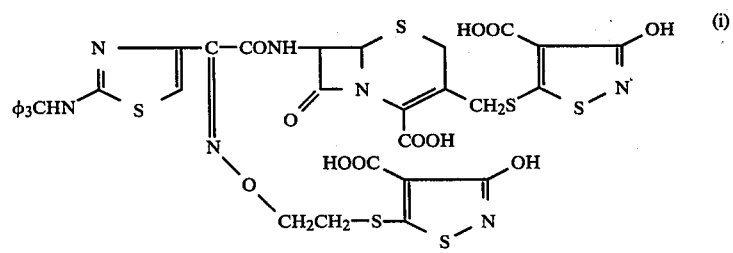

In a mixture of 2 ml of water and 3 ml of dimethylformamide was suspended 200 mg of (Z)-7-[α-(2-bromoethoxyimino)-α-(2-tritylaminothiazol-4-yl)acetamido]-3-[(4-carboxy-3-hydroxyisothiazol-5-yl)thiomethyl]-Δ³-cephem-4-carboxylic acid and then 50 mg of sodium hydrogencarbonate was added thereto and dissolved in it. To the solution was added 120 mg of 4-carboxy-3-hydroxy-5-mercaptoisothiazole tripotassium salt and the mixture was reacted for 4 hours at room temperature. After the reaction was over, 50 ml of water and 50 ml of methyl ethyl ketone were added to the reaction mixture and the pH of the mixture was adjusted to 2 by 2N hydrochloric acid with stirring under ice-cooling. The organic layer formed was recovered, washed with a saturated aqueous sodium chloride dered by the addition of ether. The powder was recovered by filtration, washed with ethanol and ether, and dried under reduced pressure to provide 60 mg of (Z)-7-{α-(2-aminothiazol-4-yl)-α-[2-(4-carboxy-3-hydroxyisothiazol-5-yl)thio]ethoxyiminoacetamido}-3-[(4-carboxy-3-hydroxyisothiazol-5-yl)thiomethyl]-Δ³-cephem-4-carboxylic acid.

Infrared absorption spectra: $\nu_{max}^{KBr}$ cm$^{-1}$: 1765, 1650

Nuclear magnetic resonance spectra (in d₆-DMSO): δ(ppm): 3.37 (2H, t) 3.63 (2H, q) 4-4.5 (4H, m) 5.20 (1H, d) 5.82 (1H, q) 6.83 (1H, s) 9.64 (1H, d)

EXAMPLE 24

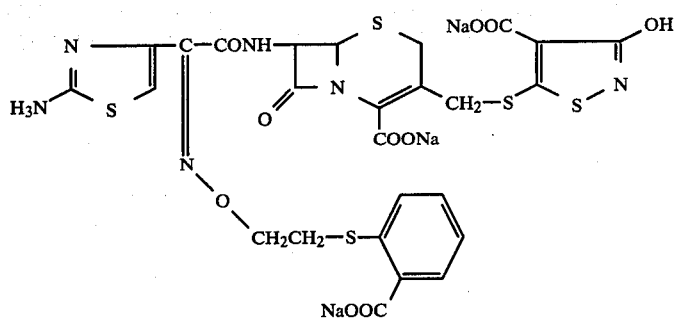

By following the same procedure as in Example 23 using and 2-mercaptobenzoic acid (Z)-7-[α-(2-bromoethoxyimino)-α-(2-trityl-aminothiazol-4-yl)acetamido]-3-[(4-carboxy-3-hydroxyisothiazol-5-yl)thiomethyl]-Δ³-cephem-4-carboxylic acid, the desired product was obtained.

Infrared absorption spectra: $\nu_{max}^{KBr}$ cm$^{-1}$: 1755, 1600

Nuclear magentic resonance spectra: δ(ppm): 3.35 (2H, t) 4.98 (1H, d) 5.76 (1H, d) 7.00 (1H, s) 7.1–8.0 (4H, m).

EXAMPLE 25

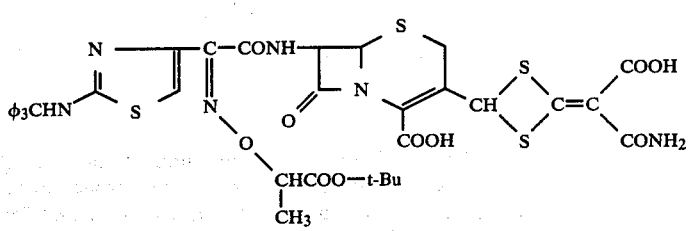

By following the same procedure as in Example 11-(i) using 510 mg of the compound obtained in Reference example 8-(iii), 5 ml of dioxane, 124 mg of 1-hydroxybenzotriazole and 190 mg of dicyclohexylcarbodiimide, a dioxane solution of an active ester was obtained. On the other hand, the aforesaid dioxane solution of the active ester was added dropwise to the mixture (solution) of 500 mg of 7-amino-3-[(4-carboxy-3-hydroxyisothiazol-5-yl)thiomethyl]-Δ³-cephem-4-carboxylic acid, 3 ml of dimethylsulfoxide and 450 μl of triethylamine to provide 335 mg of (Z)-3-[4-(1-carbonyl-1-carboxymethylene)-1,3-dithietan-2-yl]-7-[α-(tert-butoxycarbonylbenzyloxyimino)-α-(2-tritylaminothiazol-4-yl)acetamido]-Δ³-cephem-4-carboxylic acid.

Infrared absorption spectra: $\nu_{max}^{KBr}$ cm$^{-1}$: 3300–3350, 2960, 1780, 1720, 1675, 1625, 1490, 1365, 1250, 695

Nuclear magnetic resonance spectra (in d₆-DMSO) δ(ppm): 1.28 (3H, d, CH₃—) 1.37 (9H, s, —t—Bu) 3.90 (2H, s, CH₂ at 2-position) 4.50 (1H, q, $-\overset{|}{C}H-$ )

5.12 (1H, d, CH at 6-position) 5.55 (1H, d,d, CH at 7-position) 5.72 (1H, s,

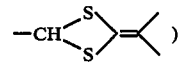

6.72 (1H, s, (i)

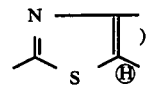

7.10–7.40 (15H, Cφ₃) 8.78 (1H, s, —NH—) 9.3–9.5 (1H, —CONH—)

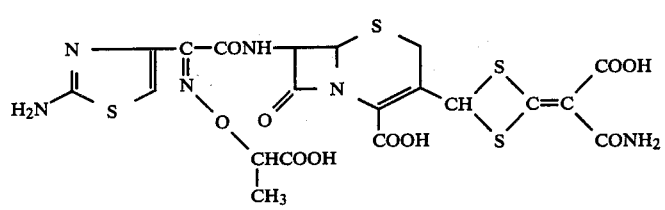

By following the same procedure as in Example 15-(ii) using 330 mg of the compound obtained in above (i), the protective group of the compound was removed with formic acid to provide 230 mg of the desired product.

Infrared absorption spectra: $\nu_{max}^{KBr}$ cm$^{-1}$: 3260–3320, 1765, 1670, 1620, 1485, 1360–1390, 1250, 1190, 1030, 795

Nuclear magnetic resonance spectra (in d₆-DMSO) δ(ppm): 1.43 (3H, d, CH₃—) 3.94 (2H, s, CH₂ at 2-position) 4.62 (1H, q, 5.17 (1H, d, CH at 6-position) 5.73 (1H, s,

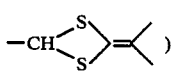)

5.8–6.0 (1H, m, CH at 7-position) 6.78 (1H, s,

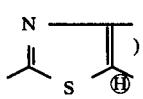)

9.46, 9.51 (1H, d(each), —CONH—)

Reference example 9

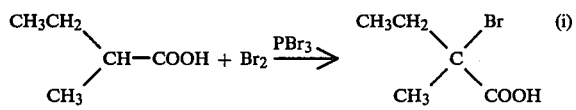

To 46.4 g of DL-2-methylbutyric acid was added dropwise 89 g (28.8 ml) of bromide at room temperature and then after adding thereto 1 ml of phosphorus tribromide, the mixture was heated to 80°–90° C. In this case, hydrogen bromide was generated. After about 3 hours, the color of bromide vanished and the generation of hydrogen bromide stopped.

After cooling the reaction mixture to room temperature, it was dispersed in 200 ml of ice-water and then extracted twice each time with 100 ml of ether. The ether layers were combined with each other and the mixture was washed twice each time with 50 ml of water and once with 50 ml of a saturated aqueous sodium chloride solution. After drying the ether layer with anhydrous magnesium sulfate, ether was distilled off to provide 82 g of an oil (2-bromo-2-methylbutyric acid).

The properties of the product oil were as follows:

Infrared absorption spectra: $v_{max}^{neat}$ cm$^{-1}$: 2970, 1700, 1450, 1270

Nuclear magnetic resonance spectra (in CDCl$_3$): δ(ppm): 1.02 (3H, t, CH$_3$—) 1.85 (3H, s, CH$_3$—) 2.17 (2H, q, —CH$_2$—) 10.32 (1H, s, —COOH)

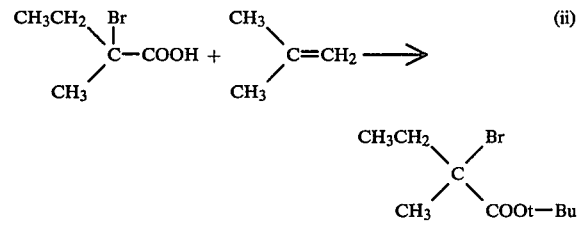

A mixture of about 40 ml of isobutene, 40 g of 2-bromo-2-methylbutyric acid, 1 ml of concentrated sulfuric acid, and 20 ml of dry ethyl ether was reacted in a closed tube overnight at room temperature. After the reaction was over, the reaction mixture was dispersed in a mixture of 150 ml of ice-water and 10 g of sodium hydrogencarbonate and extracted with 200 ml and then 100 ml of ether. The organic layers were collected, washed twice each time with 50 ml of water and then once with 50 ml of a saturated aqueous sodium chloride solution, and after drying with anhydrous magnesium sulfate, ether was distilled off to provide 36.3 g of tert-butyl 2-bromo-2-methylbutyrate.

The properties of the product were as follows:

Infrared absorption spectra: $v_{max}^{neat}$ cm$^{-1}$: 2970, 2920, 1725, 1360, 1140, 845

Nuclear magnetic resonance spectra (in CDCl$_3$): δ(ppm): 0.98 (3H, t, CH$_3$—) 1.45 (9H, s, t-Bu) 1.80 (3H, s, CH$_3$—) 2.07 (2H, q, —CH$_2$—)

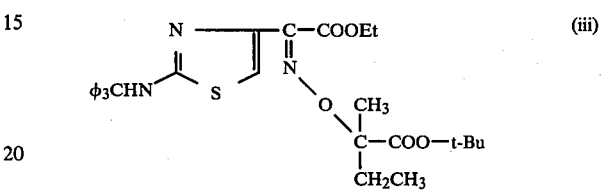 (iii)

In 150 ml of dimethyl sulfoxide was dissolved 22.43 g (45.45 millimoles) of ethyl (Z)-2-(2-tritylaminothiazol-4-yl-2-[(hydroxy)imino]butyrate hydrochloride and after adding thereto 9.1 g (65 millimoles) of powdered potassium carbonate, the reaction was performed for 30 minutes at room temperature. After the reaction was over, 12.8 g (54 millimoles) of tert-butyl 2-bromo-2-methylbutyrate was added to the reaction mixture and then the reaction was further performed overnight at room temperature. After the reaction was over, the reaction mixture was dispersed in 400 ml of ice-water and extracted with 200 ml and then 100 ml of ethyl acetate. The organic layers were collected and washed twice each time with 50 ml of water and then once with 50 ml of a saturated sodium chloride solution. After drying the ethyl acetate layer with anhydrous magnesium sulfate, the solvent was distilled off under reduced pressure and a caramel thus obtained was applied to silica gel column chromatography. The products were eluted using a mixture of n-hexane and ethyl acetate (3:1 by volume ratio) and the fractions containing the desired product were collected, the solvent was distilled off, and a caramel thus obtained was crystallized from a mixture of ether and n-hexane to provide 9.04 g of ethyl (Z)-2-(1-tert-butoxycarbonyl-1-methylpropoxyimino)-2-(2-tritylaminothiazol-4-yl)acetate having a melting point of 122°–125° C.

The properties of the product were as follows:

Infrared absorption spectra: $v_{max}^{KBr}$ cm$^{-1}$: 3260, 2960, 1730, 1530, 1515, 1290, 1130, 960, 695

Nuclear magnetic resonance spectra (in CDCl$_3$): δ(ppm): 0.88 (3H, t, CH$_3$—) 1.33 (3H, t, CH$_3$—) 1.40 (9H, s, t-Bu) 1.47 (3H, s, CH$_3$—) 1.84 (2H, q, —CH$_2$—) 4.36 (2H, q, —CH$_2$—) 6.61 (1H, s,

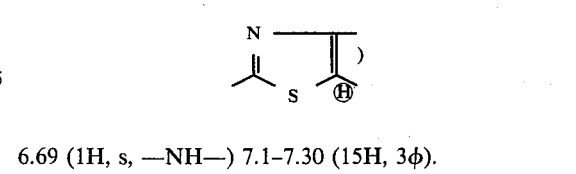)

6.69 (1H, s, —NH—) 7.1–7.30 (15H, 3φ).

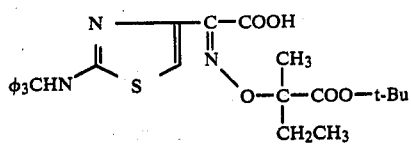 (iv)

In 495 ml of methanol was dissolved 9 g of the foregoing compound and after adding thereto a solution of 4.5 g of potassium carbonate dissolved in 55 ml of water, the reaction was performed overnight at 50°–51° C. After the reaction was over, methanol was distilled off, 50 ml of water and 25 ml of 2N hydrochloric acid were added to the aqueous solution thus obtained and then the reaction product was extracted with 200 ml and then 100 ml of ethyl acetate. The organic layers were collected and washed twice each time with 50 ml of water and then once with 50 ml of a saturated aqueous sodium chloride solution. After drying the ethyl acetate layer with anhydrous magnesium sulfate, ethyl acetate was distilled off under reduced pressure and a caramel thus obtained was applied to silica gel column chromatography. The products were eluted by a mixture of chloroform, isopropyl alcohol, and formic acid (90:10:2 by volume ratio), the fractions containing the desired product were collected, and the solvent was distilled off to provide 6.16 g of (Z)-2-(1-tert-butoxycarbonyl-1-methylpropoxyimino)2-(2-tritylaminothiazol-4-yl)acetic acid having a melting point of 163°–164° C.

The properties of the product were as follows:
Infrared absorption spectra: $\nu_{max}^{KBr}$ cm$^{-1}$: 3230, 2960, 1715, 1530, 1440, 1365, 1250, 1125, 970, 750, 735, 695

Nuclear magnetic resonance spectra (in d$_6$-DMSO): δ(ppm): 0.78 (3H, t, CH$_3$—) 1.31 (3H, s, CH$_3$—) 1.33 (9H, s, t-Bu) 1.67 (2H, q, —CH$_2$—) 6.74 (1H, s,

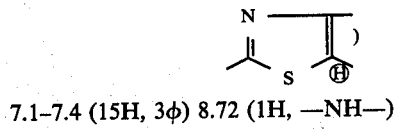

7.1–7.4 (15H, 3φ) 8.72 (1H, —NH—)

EXAMPLE 26 millimoles) of 7-amino-3-[(4-carboxy-3-hydroxyisothiazol-5-yl)thiomethyl]-Δ$^3$-cephem-4-carboxylic acid was suspended in 30 ml of water and 650 mg of sodium hydrogencarbonate was added little by little to the suspension to dissolve the suspended material. To the brown transparent solution thus obtained was added dropwise the aforesaid dioxane solution of active ester and they were reacted overnight at room temperature. The reaction mixture was subjected to distillation under reduced pressure to remove dioxane and after adding 50 ml of water and 20 ml of a saturated aqueous sodium hydrogencarbonate solution to the residue thus obtained, the mixture was washed with 100 ml and then 50 ml of ethyl acetate. To the aqueous layer thus obtained was added 30 ml of 2N hydrochloric acid and then the product was extracted with 100 ml and then 50 ml of methyl ethyl ketone. In this case, the unreacted materials precipitated during the foregoing operation were removed by filtration. The methyl ethyl ketone extract was washed twice each time with 50 ml of water and then once with 50 ml of a saturated aqueous sodium chloride solution and after drying with anhydrous magnesium sulfate, methyl ethyl ketone was distilled off under reduced pressure to provide a caramel. The caramel was applied to silica gel column chromatography, products were eluted by a mixture of chloroform, isopropyl alcohol, and formic acid (90:10:2 by volume ratio), the fractions containing the desired product were collected, the solvent was distilled off, and then the product was powdered by ether to provide 950 mg of (Z)-3-[(4-carboxy-3-hydroxyisothiazol-5-yl)thiomethyl]-7-[α-(1-tert-butoxycarbonyl-1-methylpropoxyimino)-α-(2-tritylaminothiazol-4-yl)acetamido]-Δ$^3$-cephem-4-carboxylic acid.

The properties of the product were as follows:
Infrared absorption spectra:
$\nu_{max}^{KBr}$ cm$^{-1}$: 3300–3350, 3200–3240, 2900, 1780, 1710, 1670, 1590, 1485, 1440, 1365, 1250, 1130, 995, 750, 695

Nuclear magnetic resonance spectra (in d$_6$-DMSO) δ(ppm): 0.84 (3H, t, CH$_3$—) 1.22 (3H, s, CH$_3$—) 1.39 (9H, s, t-Bu) 1.71 (2H, q, —CH$_2$—) 4.16 (2H, q, 3-position CH$_2$) 5.13 (1H, d, 6-position CH) 5.71 (1H, q, 7-position CH) 6.64 (1H, s,

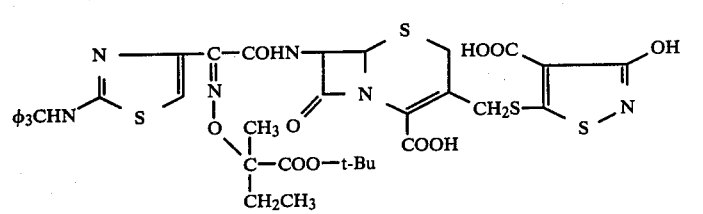 (i)

To 46 ml of dioxane were added 4.68 g (8 millimoles) of (Z)-2-(1-tert-butoxycarbonyl-1-methylpropoxyimino)-2-(2-tritylaminothiazol-4-yl)acetic acid, 1.1 g (8.15 millimoles) of 1-hydroxybenzotriazole, and 2 g (9.7 millimoles) of dicyclohexylcarbodiimide and the reaction was performed for one hour at room temperature. After the reaction was over, dicyclohexyl urea was precipitated and filtered away to provide a dioxane solution of an active ester. On the other hand, 3 g (7.7

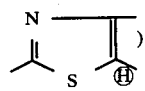

7.1–7.4 (15H, 3φ) 8.72 (1H, s, —NH—) 9.27 (1H, d, —CONH—)

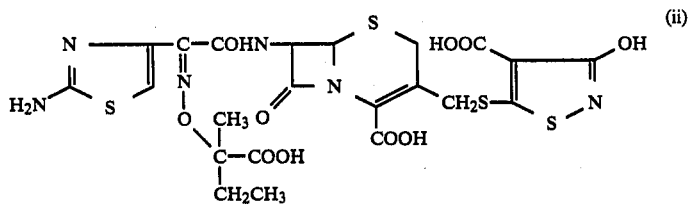 (ii)

To a mixture of 10 ml of trifluoroacetic acid and 0.5 ml of anisole was added 465 mg of the compound obtained in step (i) and the reaction was performed for one hour at 19°–21° C. After the reaction was over, trifluoroacetic acid was distilled off under reduced pressure and the oil thus obtained was powdered with ether. The powder was recovered by filtration and added to 10 ml of trifluoroacetic acid at lower than 20° C. To the mixture was added 5 ml of water at lower than 20° C. and the reaction was performed for one hour at 19°–21° C. After the reaction was over, trifluoroacetic acid and water were distilled off under reduced pressure and the residue was homogenized with the addition of 10 ml of ethanol. Then, a part of ethanol was distilled off and the oil thus obtained was powdered by the addition of ethyl ether to provide 330 mg of (Z)-7-[α-(2-aminothiazol-4-yl)-α-(1-carboxy-1-methylpropoxyimino)acetamido]-3-[(4-carboxy-3-hydroxyisothiazol-5-yl)thiomethyl]-Δ³-cephem-4-carboxylic acid.

The properties of the product were as follows:
Infrared absorption spectra: $\nu_{max}^{KBr}$ cm$^{-1}$: 3300–3400, 1770, 1620, 1120, 1000, 790, 720

Nuclear magnetic resonance spectra (in d$_6$-DMSO) δ(ppm): 0.86 (3H, t, CH$_3$—) 1.38, 1.41 (3H, each s, CH$_3$—) 1.82 (2H, q, —CH$_2$—) 3.68 (2H, q, 2-position CH$_2$) 4.18 (2H, q, —CH$_2$—S—) 5.18 (1H, d, 6-position CH) 5.7–5.9 (1H, 7-position CH) 6.71 (1H, s,

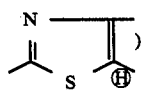

7.28 (1H, —NH—) 9.36 (1H, d, —CONH—).

reaction mixture under reduced pressure, the residue thus obtained was dispersed in 10 ml of ice-water and after adding thereto 5 ml of 2N hydrochloric acid, the product was extracted twice each time with 20 ml of methyl ethyl ketone. The organic layers were combined with each other and washed with 5 ml of water and then 10 ml of a saturated aqueous sodium chloride solution. After drying the methyl ethyl ketone layer by anhydrous magnesium sulfate, the solvent was distilled off and the caramel thus formed was applied to silica gel column chromatography. Products were eluted with a mixture of chloroform, isopropyl alcohol, and formic acid (90:10:2 by volume ratio) and the fractions containing the desired product were collected and concentrated under reduced pressure to provide 245 mg of (Z)-3-[(4-carbamoylcarboxymethylene)-1,3-dithiethan-2-yl]-7-[α-(1-tert-butoxycarbonyl-1-methylpropoxyimino)-α-(2-tritylaminothiazol-4-yl)acetamido]-Δ³-cephem-4-carboxylic acid.

The properties of the product were as follows:
Infrared absorption spectra: $\lambda_{max}^{KBr}$ cm$^{-1}$: 3300–3400, 2970, 1770, 1670, 1620, 1490, 1365, 1255, 1140, 700

Nuclear magnetic resonance spectra (in d$_6$-DMSO) δ(ppm): 0.91 (3H, t, CH$_3$—) 1.40 (9H, 3H, s, t-Bu, CH$_3$—) 1.90 (2H, q, —CH$_2$—) 3.98 (2H, 2-position CH) 5.07 (1H, d, 6-position CH) 5.90, 5.94 (1H, each s,

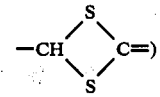

5.8–5.96 (1H, 7-position CH) 6.68 (1H, s,

EXAMPLE 27

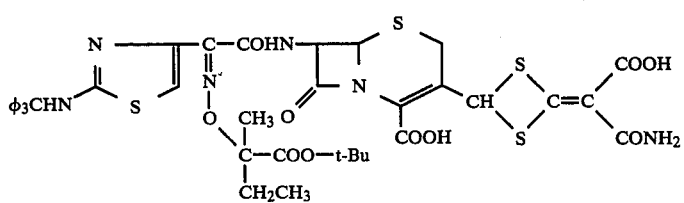 (i)

In 3 ml of dimethyl sulfoxide was dissolved 460 mg (0.477 millimole) of the compound obtained in Example 26 (i) and 10 ml of dioxane was added to the solution. Then, after adding 250 μl of triethylamine at room temperature, the reaction was performed for 4 days at room temperature. Dioxane was distilled off from the

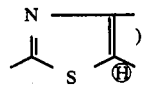

7.1–7.4 (15H, 3φ) 8.50 (1H, —NH—)

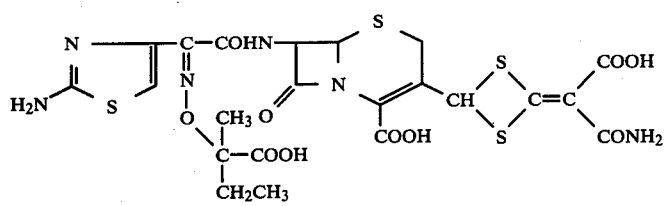

To a mixture of 9 ml of trifluoroacetic acid and 1 ml of anisole was added 240 mg of the foregoing compound and the reaction was performed for one hour at 19°–21° C. After the reaction was over, trifluoroacetic acid was distilled off under reduced pressure and the oil thus obtained was powdered by the addition of ether. The powder obtained by filtration was dissolved again in 7 ml of trifluoroacetic acid and 4 ml of water was added dropwise to the solution at temperature below 20° C. Thereafter, the reaction was performed for one hour at 19°–21° C. After the reaction was over, trifluoroacetic acid was distilled off and the residue was homogenized by the addition of 10 ml of ethanol. A part of ethanol was distilled off and the oil thus obtained was powdered by the addition of ethyl ether to provide 146 mg of (Z)-3-[(4-carbamoylcarboxymethylene)-1,3-dithiethan-2-yl]-7-[α-(1-carboxy-1-methylpropoxyimino)-α-(2-aminothiazol-4-yl)acetamido]-Δ³-cephem-4-carboxylic acid.

The properties of the product were as follows:

Infrared absorption spectra: $\nu_{max}^{KBr}$ cm$^{-1}$: 3300, 2960, 1765, 1490, 1370, 1260, 1140, 1000, 800, 720

Nuclear magnetic resonance spectra (in d$_6$-DMSO): δ(ppm): 0.85 (3H, t, CH$_3$—) 1.38, 1.40 (3H, each s, CH$_3$—) 1.77 (2H, q, —CH$_2$—) 3.93 (2H, 2-position CH$_2$) 5.15 (1H, d, 6-position CH) 5.72 (1H, s,

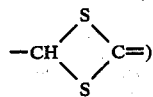

5.88 (1H, q, 7-position CH) 6.69 (1H, s,

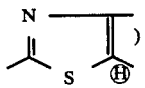

9.44 (1H, d, —CONH—)

REFERENCE EXAMPLE 10

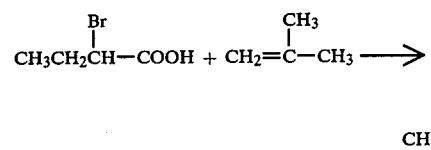

By following the same procedure as in Reference example 9(ii), 29 g of tert-butyl α-bromobutyrate was obtained from 25 g of α-bromo-n-butyric acid.

The properties of the product were as follows:

Infrared absorption spectra: $\nu_{max}^{neat}$ cm$^{-1}$: 2960, 1725, 1360, 1140, 840

Nuclear magnetic resonance spectra (in CDCl$_3$): δ(ppm): 0.98 (3H, t, CH$_3$—) 1.46 (9H, s, t-Bu) 1.91 (2H, q, —CH$_2$—) 4.00 (1H, t,

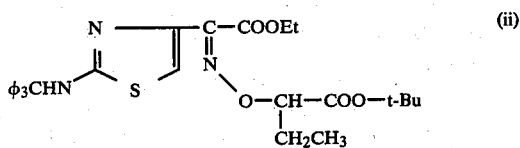

By following the same procedure as in Reference example 9(iii) ethyl (Z)-2-(1-tert-butoxycarbonylpropoxyimino)-2-(2-(tritylaminothiazol-4-yl)acetate was obtained from tert-butyl-α-bromobutyrate and ethyl (Z)-2-hydroxyimino-2-(2-tritylaminothiazol-4-yl)acetate hydrochloride.

The properties of the product were as follows:

Infrared absorption spectra: $\nu_{max}^{KBr}$ cm$^{-1}$: 3320–3370, 2960, 1730, 1525, 1270, 1180, 1150, 1025, 990, 690

Nuclear magnetic resonance spectra (in CDCl$_3$): δ(ppm): 0.96 (3H, t, CH$_3$—) 1.35 (3H, t, CH$_3$—) 1.44 (9H, s, t-Bu) 1.85 (2H, m, —CH$_2$—) 4.38 (2H, q, —CH$_2$—) 4.68 (1H, t,

6.56 (1H, s,

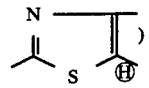

6.93 (1H, s, —NH—) 7.30 (15H, s, 3φ)

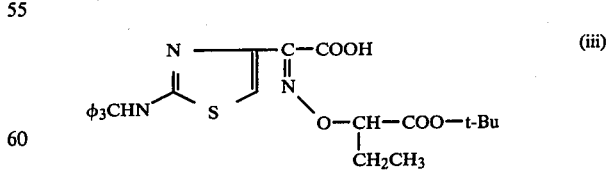

By following the same procedure as in Reference example 9(iv), the desired product was obtained from ethyl (Z)-2-(1-tert-butoxycarbonylpropoxyimino)-2-(2-tritylaminothiazol-4-yl)acetate. Melting point: 172°–173° C. (decompd.)

The properties of the product were as follows:

Infrared absorption spectra: $\nu_{max}^{KBr}$ cm$^{-1}$: 3250, 2960, 1715, 1530, 1430, 1355, 1245, 1150, 1130, 990, 840, 690

Nuclear magnetic resonance spectra (in d$_6$-DMSO) δ(ppm): 0.90 (3H, t, CH$_3$—) 1.40 (9H, s, t-Bu) 1.64 (2H, q, —CH$_2$—) 4.42 (1H, s, $$-\overset{|}{\underset{|}{C}}H-)$$

6.84 (1H, s, 5.20 (1H, d, 6-position CH) 5.64–5.80 (1H, 7-position CH) 6.74, 6.78 (1H, each s,

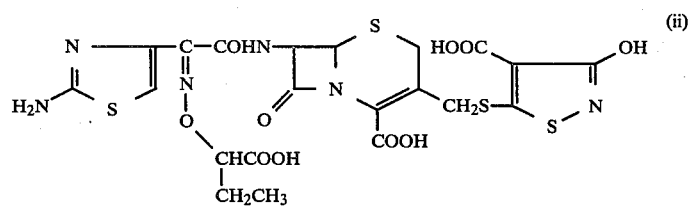

7.1–7.5 (15H, 3φ)

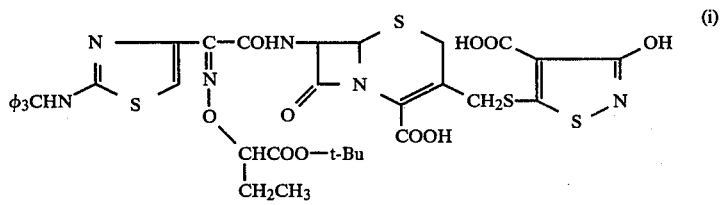

7.1–7.5 (15H, 3φ) 8.81 (1H, s, —NH—)

EXAMPLE 28

By following the same procedure as in Example 26(i), (Z)-3-[4-carboxy-3-hydroxyisothiazol-5-yl)thiomethyl]-7-[α-(1-tert-butoxycarbonylpropoxyimino)-α-(2-tritylaminothiazol-4-yl)acetamido]-Δ$^3$-cephem-4-carboxylic acid was obtained from (Z)-2-(1-tert-butoxycarbonylpropoxyimino)-2-(2-tritylaminothiazol-4-yl)acetic acid and 7-amino-3-[(4-carboxy-3-hydroxyisothiazol-5-yl)thiomethyl]-Δ$^3$-cephem-4-carboxylic acid.

The properties of the product were as follows:
Infrared absorption spectra: $\nu_{max}^{KBr}$ cm$^{-1}$: 3300, 2920, 1775, 1715, 1670, 1615, 1440, 1360, 1240, 1150, 995, 690

Nuclear magnetic resonance spectra: (in d$_6$-DMSO) δ(ppm): 0.96 (3H, t, CH$_3$—) 1.44 (9H, t, t-Bu) 1.70 (2H, q, —CH$_2$—) 3.63 (2H, q, 2-position CH$_2$) 4.49 (1H, t, By following the same procedure as in Example 26(ii), the desired product was obtained from (Z)-3-[(4-carboxy-3-hydroxyisothiazol-5-yl)thiomethyl]-7-[α-(1-tert-butoxycarbonylpropoxyimino)-α-(2-tritylaminothiazol-4-yl)acetamido]-Δ$^3$-cephem-4-carboxylic acid.

The properties of the product were as follows:
Infrared absorption spectra: $\nu_{max}^{KBr}$ cm$^{-1}$: 3280–3370, 1765, 1660, 1620, 1185, 1000, 790, 720

Nuclear magnetic resonance spectra: (in d$_6$-DMSO): δ(ppm): 0.96 (3H, t, CH$_3$—) 1.81 (2H, q, —CH$_2$—) 3.68 (2H, q, 2-position CH$_2$) 4.22 (2H, q, —CH$_2$S—) 4.49 (1H, t, $$-\overset{|}{\underset{|}{C}}H-)$$

5.21 (1H, d, 6-position CH) 5.90 (1H, q, 7-position CH) 6.76, 6.78 (1H, each s, 9.46, 9.48 (1H, each d, —CONH—)

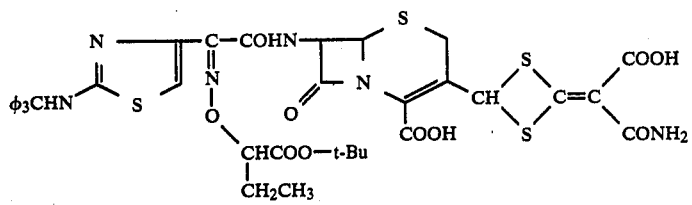

By following the same procedure as in Example 27(i), (Z)-3-[(4-carbamoylcarboxymethylene)-1,3-dithiethan-2-yl]-7-[α-(1-tert-butoxycarbonylpropoxyimino)-α-(2-tritylaminothiazoi-4-yl)acetamido]-Δ³-cephem-4-carboxylic acid was obtained from (Z)-3-[(4-carboxy-3-hydroxyisothiazol-5-yl)thiomethyl]-7-[α-(tert-butoxycarbonylpropoxyimino)-α-(2-tritylaminothiazol-4-yl)acetamido]-Δ³-cephem-4-carboxylic acid.

The properties of the product were as follows:
$\nu_{max}^{KBr}$ cm$^{-1}$: 3280-3330, 2960, 1770, 1670, 1620, 1485, 1360, 1230, 1150, 995, 690

Nuclear magnetic resonance spectra (in d$_6$-DMSO): δ(ppm): 0.94 (3H, t, CH$_3$—) 1.38 (9H, s, t-Bu) 1.76 (2H, q, —CH$_2$—) 3.91 (2H, 2-position CH$_2$) 4.34 (1H, t,

5.16 (1H, d, 6-position CH) 5.74 (1H, s,

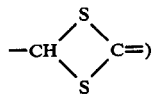

5.70–5.8 (1H, 7-position CH) 6.72, 6.77 (1H, each, s,

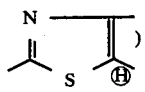

7.1–7.5 (15H, 3φ) 8.80 (1H, —NH—) 9.3–9.5 (1H, —CONH—)

bonylpropoxyimino)-α-(2-tritylaminothiazol-4-yl)acetamido]-Δ³-cephem-4-carboxylic acid.

The properties of the product were as follows:
Infrared absorption spectra: $\nu_{max}^{KBr}$ cm$^{-1}$: 3250-3339, 2950, 1770, 1620, 1480, 1370, 1250, 1000

Nuclear magnetic resonance spectra (in d$_6$-DMSO): δ(ppm): 0.98 (3H, t, CH$_3$—) 1.82 (2H, q, —CH$_2$—) 3.96 (2H, 2-position CH) 4.50 (1H,

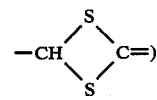

5.18 (1H, d, 6-position CH) 5.75 (1H, s,

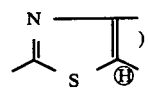

5.8–6.0 (1H, m, 7-position CH) 6.78, 6.82 (1H, each s,

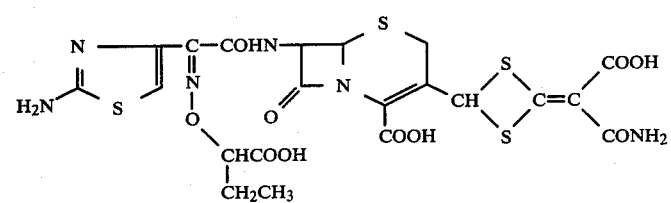

9.40–9.60 (1H, —CONH—)

EXAMPLE 30

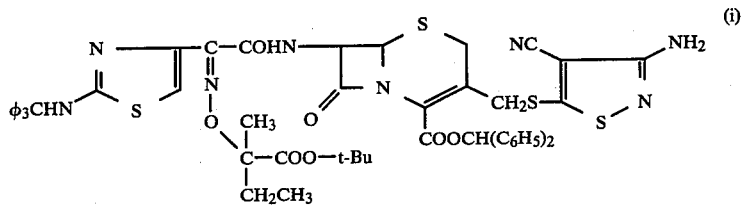

A mixture of 5.85 g (0.01 mole) of (Z)-2-(1-tert-butoxycarbonyl-1-methylpropoxyimino)-2-(2-tritylaminothiazol-4-yl)acetic acid obtained in Reference example 9(iv), 1.35 g (0.01 mole) of 1-hydroxybenztriazole, 2.06 g (0.01 mole) of dicyclohexylcarbodiimide, and 50 ml of dioxane was stirred for one hour at room temperature. The reaction mixture was filtered to remove dicyclohexylurea. The filtrate was added dropwise to a By following the same procedure as in Example 27(ii), the desired product was obtained by removing the protective group of (Z)-3-[(4-carbamoylcarboxymethylene)-1,3-dithiethan-2-yl]-7-[α-(1-tert-butoxycarmixture of 3.7 g (0.01 mole) of 7-amino-3-[(3-amino-4-cyanoisothiazol-5-yl)thiomethyl]-Δ³-cephem-4-carboxylic acid obtained in Reference example 3, 1.68 g (0.02 mole) of sodium hydrogencarbonate, and 50 ml of water. After stirring the mixture overnight at room temperature, 100 ml of water and 200 ml of ethyl acetate were added thereto and the pH of the resultant mixture was adjusted to 2 with 2N hydrochloric acid with stirring under ice-cooling.

Insoluble matters precipitated were filtered away and the ethyl acetate layer was recovered, washed twice each time with 50 ml of a saturated sodium chloride solution, and after drying by anhydrous magnesium sulfate, concentrated under reduced pressure. The concentrated residue was dissolved in 40 ml of methylene chloride and after adding thereto 1.0 g of diphenyldiazomethane, and the resultant mixture was stirred for one hour at room temperature. The reaction mixture was concentrated and applied to silica gel column chromatography. Products were eluted by a mixture of benzene and ethyl acetate (90:10 by volume ratio) and the fractions containing the desired product were collected and concentrated to provide 900 mg of (Z)-3-[(3-amino-4-cyanoisothiazol-5-yl)thiomethyl]-7-[α-(1-tert-butoxycarbonyl-1-methylpropoxyimino)-α-(2-tritylaminothiazol-4-yl)acetamido]-Δ³-cephem-4-carboxylic acid benzhydryl ester.

The properties of the product were as follows:
Infrared absorption spectra: $\nu_{max}^{KBr}$ cm$^{-1}$: 2205, 1780, 1720, 1680

Nuclear magnetic resonance spectra (in CDCl₃): δ(ppm): 0.97 (3H, t, —CH₃) 1.43 (9H, s, t-Bu) 1.57, 1.62 (3H, each s, —CH₃) 1.98 (2H, q, —CH₂—) 3.54 (2H, q, 2-position CH₂) 4.07 (2H, q, 3-position CH₂) 5.03 (1H, d, 6-position H) 5.96 (1H, d, q, 7position H) 6.75 (1H, s, 6.92 (1H, s,

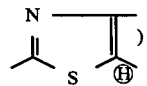

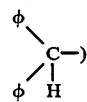

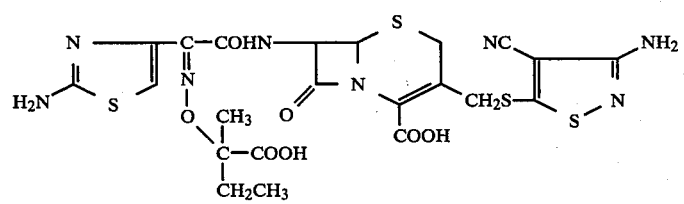

To 900 mg of the compound in foregoing step (i) were added 0.5 ml of anisole and 5 ml of trifluoroacetic acid under ice-cooling, after stirring the mixture for 2 hours at room temperature, 2 ml of water was added, and the resultant mixture was further stirred for 2 hours at room temperature. The reaction mixture was concentrated under reduced pressure and the residue was powdered by the treatment with ether. The powder thus obtained was recovered by filtration, washed with ether, and dried under reduced pressure to provide 250 mg of (Z)-3-[(3-amino-4-cyanoisothiazol-5-yl)thiomethyl]-7-[α-(2-aminothiazol-4-yl)-α-(1-carboxy-1-methylpropoxyimino)acetamido]-Δ³-cephem-4-carboxylic acid.

The properties of the product were as follows:
Infrared absorption spectra: $\nu_{max}^{KBr}$ cm$^{-1}$: 2205, 1770

Nuclear magnetic resonance spectra (in d₆-DMSO): δ(ppm): 0.88 (3H, t, —CH₃) 1.42, 1.44 (3H, each s, —CH₃) 1.84 (2H, q, —CH₂—) 3.70 (2H, q, 2-position CH₂) 4.32 (2H, q, 3-position CH₂) 5.21 (1H, d, 6-position CH) 5.83 (1H, dd, 7-position CH) 6.75, 6.77 (1H, each s,

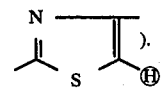

What is claimed:

1. A cephalosporin compound represented by the formula

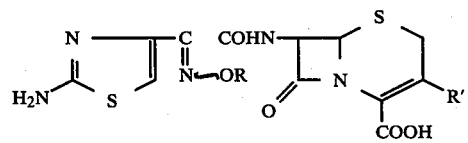

wherein R represents a group of the formula

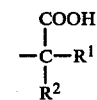

(wherein R¹ represents a hydrogen atom or a lower alkyl group of 1-3 carbon atoms and R² represents a hydrogen atom, a lower alkyl group of 1-3 carbon atoms, a phenyl group which may be substituted by an amino or hydroxy group, a cyano group, a carboxy group, or a carboxymethyl group; said R¹ and R² may form a cycloalkylidene group of 4-6 carbon atoms together with the carbon atom to which they are bonded) or a group of the formula —CH₂—R³ (wherein R³ represents a hydrogen atom, a halogenomethyl group, a carbamoyl group, a carboxymethyl group, a 4-carboxy-3-hydroxyisothiazol-5-yl-thiomethyl group; or a 2-carboxyphenylthiomethyl group); R' represents a group of the formula

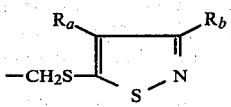

(wherein $R_a$ represents a carboxy group, a cyano group, or a carbamoyl group which may be substituted by a lower alkyl group of 1–3 carbon atoms and $R_b$ represents a hydroxy group or an amino group) or a group of the formula

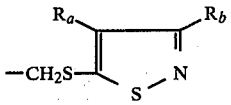

(wherein $R_a$ and $R_b$ have the same significance as above); and the waveline ∼ shows an anti-form or syn-form bond and the salts thereof.

2. The cephalosporin compound of claim 1, which is 7-[α-(2-Aminothiazol-4-yl)-α-(1-carboxy-1-methylethoxyimino)acetamido]-3-[(4-carboxy-3-hydroxyisothiazol-5-yl)thiomethyl]-Δ³-cephem-4-carboxylic acid.

3. The cephalosporin compound of claim 1, which is 7-[α-(2-Aminothiazol-4-yl)-α-(1-carboxycyclobut-1-yloxyimino)acetamido]-3-[(4-carboxy-3-hydroxyisothiazol-5-yl)thiomethyl]-Δ³-cephem-4-carboxylic acid.

4. The cephalosporin compound of claim 1, which is 7-[α-(2-Aminothiazol-4-yl)-α-(1-carboxycyclopent-1-yloxyimino)acetamido]-3-[(4-carboxy-3-hydroxyisothiazol-5-yl)thiomethyl]-Δ³-cephem-4-carboxylic acid.

5. The cephalosporin compound of claim 1, which is 7-[α-(2-Aminothiazol-4-yl)-α-(α-carboxybenzyloxyimino)acetamido]-3-[(4-carboxy-3-hydroxyisothiazol-5-yl)thiomethyl]-Δ³-cephem-4-carboxylic acid.

6. The cephalosporin compound of claim 1, wherein R' is

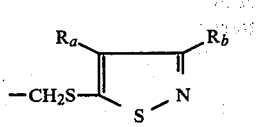

$R_b$ represents a hydroxy group or an amino group, and $R_a$ is as defined in claim 1.

7. The cephalosporin compound of claim 1, wherein R' is

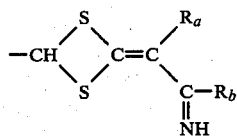

$R_b$ represents a hydroxy group or an amino group, and $R_a$ is as defined in claim 1.

8. An antibiotic composition comprising an effective amount of the compound of claim 1 and a pharmaceutically acceptable excipient or diluent thereof.

* * * * *